(12) United States Patent
Schmulenson et al.

(10) Patent No.: US 9,354,506 B2
(45) Date of Patent: *May 31, 2016

(54) RADIATION SENSING DEVICE AND HOLDER

(76) Inventors: Harold K. Schmulenson, Buffalo Grove, IL (US); Tom Gillen, Orland Park, IL (US)

(*) Notice: Subject to any disclaimer, the term of this patent is extended or adjusted under 35 U.S.C. 154(b) by 873 days.

This patent is subject to a terminal disclaimer.

(21) Appl. No.: 13/397,557

(22) Filed: Feb. 15, 2012

(65) Prior Publication Data

US 2012/0148030 A1   Jun. 14, 2012

Related U.S. Application Data

(63) Continuation of application No. 12/345,303, filed on Dec. 29, 2008, now Pat. No. 8,142,074, which is a continuation-in-part of application No. 11/945,215, filed on Nov. 26, 2007, now Pat. No. 7,819,579.

(51) Int. Cl.
*G03B 42/04* (2006.01)
*A61B 6/14* (2006.01)
*A61B 6/00* (2006.01)

(52) U.S. Cl.
CPC .............. *G03B 42/042* (2013.01); *A61B 6/145* (2013.01); *A61B 6/4435* (2013.01)

(58) Field of Classification Search
CPC ..... A61B 6/145; A61B 6/4435; G03B 42/042
USPC ......................... 378/168–170, 191
See application file for complete search history.

(56) References Cited

U.S. PATENT DOCUMENTS

| | | | |
|---|---|---|---|
| 1,434,894 A | 11/1922 | Hawkings |
| 1,557,796 A | 10/1925 | Bonar et al. |
| 1,706,117 A | 3/1929 | Heckel |
| 2,005,993 A | 8/1935 | Heron et al. |
| 2,075,491 A | 3/1937 | Wilson |
| 2,090,933 A | 8/1937 | Bolin et al. |
| 2,239,569 A | 4/1941 | Poindexter |
| 2,240,336 A | 4/1941 | Kreider |
| 2,565,823 A | 8/1951 | Pool |
| 3,304,422 A | 2/1967 | Norback et al. |
| 3,356,845 A | 12/1967 | Bergendal |
| 3,473,026 A | 10/1969 | Updegrave |

(Continued)

FOREIGN PATENT DOCUMENTS

DE            8701308            3/1987

OTHER PUBLICATIONS

Uni-bite Film Holder—Unident "American Dental Accessories Catalog"—Summer 2005.

(Continued)

*Primary Examiner* — Toan Ton
*Assistant Examiner* — Mona M Sanei
(74) *Attorney, Agent, or Firm* — Klintworth & Rozenblat IP LLC

(57) ABSTRACT

A system for holding and aligning a radiation sensing device is described. The system includes a radiation sensing device having a sensor engagement member. The system also includes a holder having a retention member including first and second retention guides connected with opposing ends of a back plate. The first retention guide also includes a complementary holder engagement member configured to mate with the sensor engagement member at a preset position.

14 Claims, 27 Drawing Sheets

(56) References Cited

U.S. PATENT DOCUMENTS

| | | | |
|---|---|---|---|
| 4,075,494 A | 2/1978 | Jermyn | |
| 4,150,296 A | 4/1979 | Edeland et al. | |
| 4,251,732 A | 2/1981 | Fried | |
| 4,295,050 A | 10/1981 | Linden | |
| 4,365,162 A | 12/1982 | Jarby | |
| 4,484,342 A | 11/1984 | Allison et al. | |
| 4,489,427 A | 12/1984 | Allison et al. | |
| 4,554,676 A | 11/1985 | Maldonado et al. | |
| 4,707,847 A | 11/1987 | Van Aken | |
| 4,815,117 A | 3/1989 | Waldo | |
| 4,866,750 A | 9/1989 | Chavarria et al. | |
| 4,945,553 A | 7/1990 | Willis | |
| 4,949,370 A | 8/1990 | Tanaka | |
| 4,965,885 A | 10/1990 | Fuhrmann | |
| 5,022,065 A | 6/1991 | Wijkstrom | |
| 5,044,009 A | 8/1991 | Klauser | |
| 5,090,047 A | 2/1992 | Angotti et al. | |
| 5,161,971 A | 11/1992 | Neiner et al. | |
| 5,289,522 A | 2/1994 | Kanbar et al. | |
| 5,327,477 A | 7/1994 | Levy | |
| 5,364,602 A | 11/1994 | Leduc | |
| 5,473,662 A | 12/1995 | Barish | |
| 5,625,666 A | 4/1997 | Willis | |
| 5,629,972 A | 5/1997 | Hausmann et al. | |
| 5,652,779 A | 7/1997 | Levy et al. | |
| 5,677,537 A | 10/1997 | Pfeiffer | |
| 5,737,388 A | 4/1998 | Kossila | |
| 5,799,058 A | 8/1998 | Willis et al. | |
| 6,033,111 A | 3/2000 | Winters et al. | |
| 6,102,566 A | 8/2000 | Willis | |
| 6,159,007 A | 12/2000 | Sorensen | |
| 6,190,042 B1 | 2/2001 | Dove et al. | |
| 6,343,875 B1 | 2/2002 | Eppinger et al. | |
| 6,363,949 B1 | 4/2002 | Brown | |
| 6,461,038 B2 | 10/2002 | Pellegrini et al. | |
| 6,540,399 B1 | 4/2003 | Eppinger et al. | |
| 6,592,256 B2 | 7/2003 | Da Rold et al. | |
| 6,905,244 B2 | 6/2005 | Kilcher et al. | |
| 6,932,505 B2 | 8/2005 | Yao et al. | |
| 7,226,208 B2 | 6/2007 | Schmulenson | |
| 8,142,074 B2 * | 3/2012 | Schmulenson et al. | 378/170 |
| 2002/0076002 A1 | 6/2002 | Eppinger et al. | |
| 2002/0106057 A1 | 8/2002 | Halpert | |
| 2003/0047589 A1 | 3/2003 | Fujii | |
| 2003/0185347 A1 | 10/2003 | Diederich | |
| 2004/0028187 A1 | 2/2004 | Diederich | |
| 2004/0154256 A1 | 8/2004 | Kim | |
| 2004/0170253 A1 | 9/2004 | Landis et al. | |
| 2005/0013412 A1 | 1/2005 | Calderwood et al. | |
| 2005/0047550 A1 | 3/2005 | Yao et al. | |
| 2006/0188070 A1 | 8/2006 | Razzano et al. | |
| 2007/0280424 A1 | 12/2007 | Schmulenson et al. | |
| 2008/0025468 A1 | 1/2008 | Schmulenson et al. | |
| 2010/0126658 A1 | 5/2010 | De Vita et al. | |

OTHER PUBLICATIONS

X-Ray Holders—"American Dental Accessories Catalog"—Summer 2005.

Sensor-Pro Digital Sensor Holder—Op-de_Op Sensor Pro—"American Dental Accessories Catalog"—Summer 2005.

Sensor and X-Ray Holder—Dec. 2004—Dentsipy/Rinn Snap A Ray.

Sensor Mounted in X-Ray Holder—Dec. 2004—Dentsipy/Rinn Snap A Ray.

Sensor (black) Next to Standard X-Ray—Dec. 2004—Dentsipy/Rinn Snap A Ray.

International Search Report and Written Opinion dated Feb. 14, 2006 for PCT application No. PCT/US2005/040854.

International Search Report and Written Opinion dated Mar. 5, 2007 for PCT application No. PCT/US2006/033028.

* cited by examiner

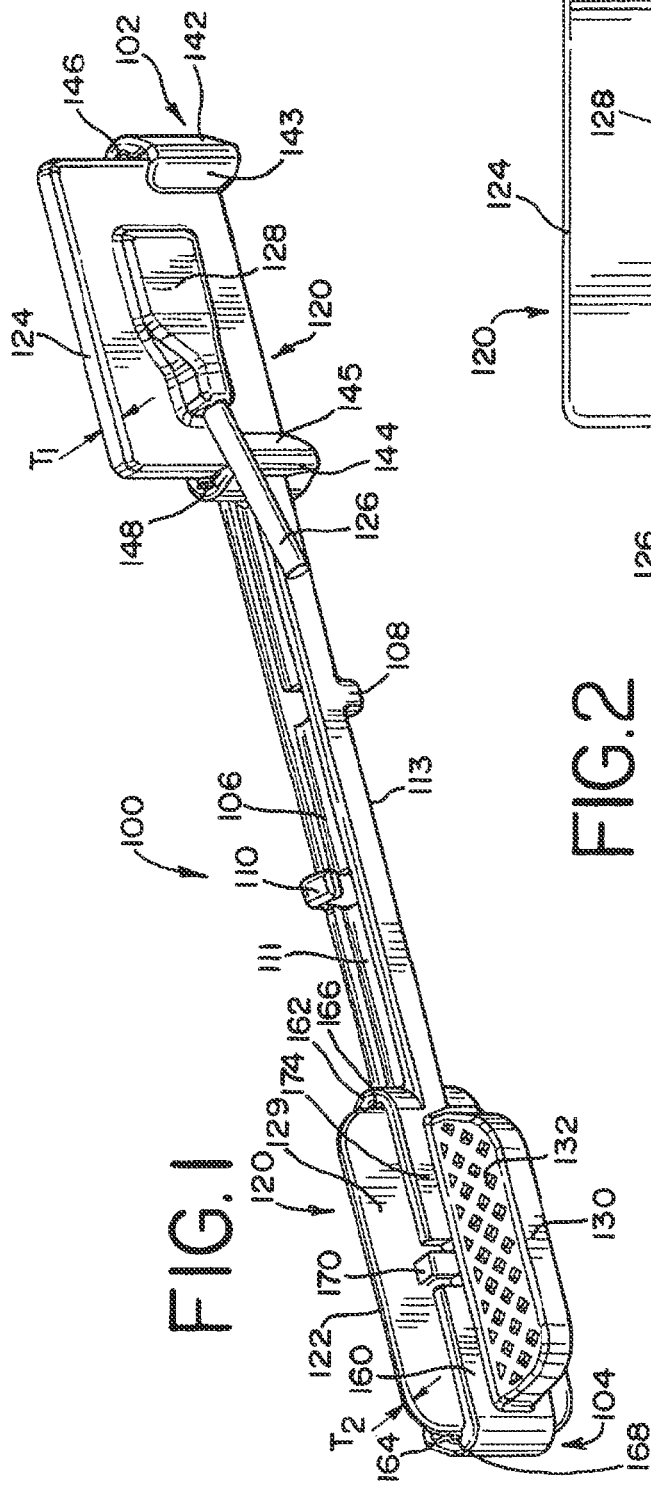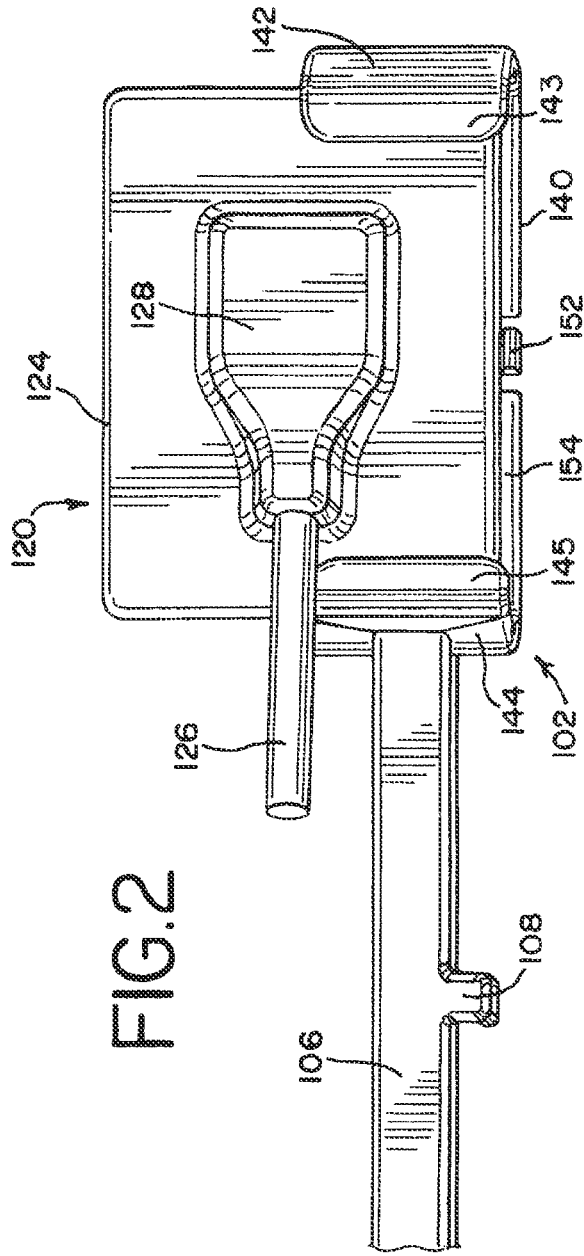

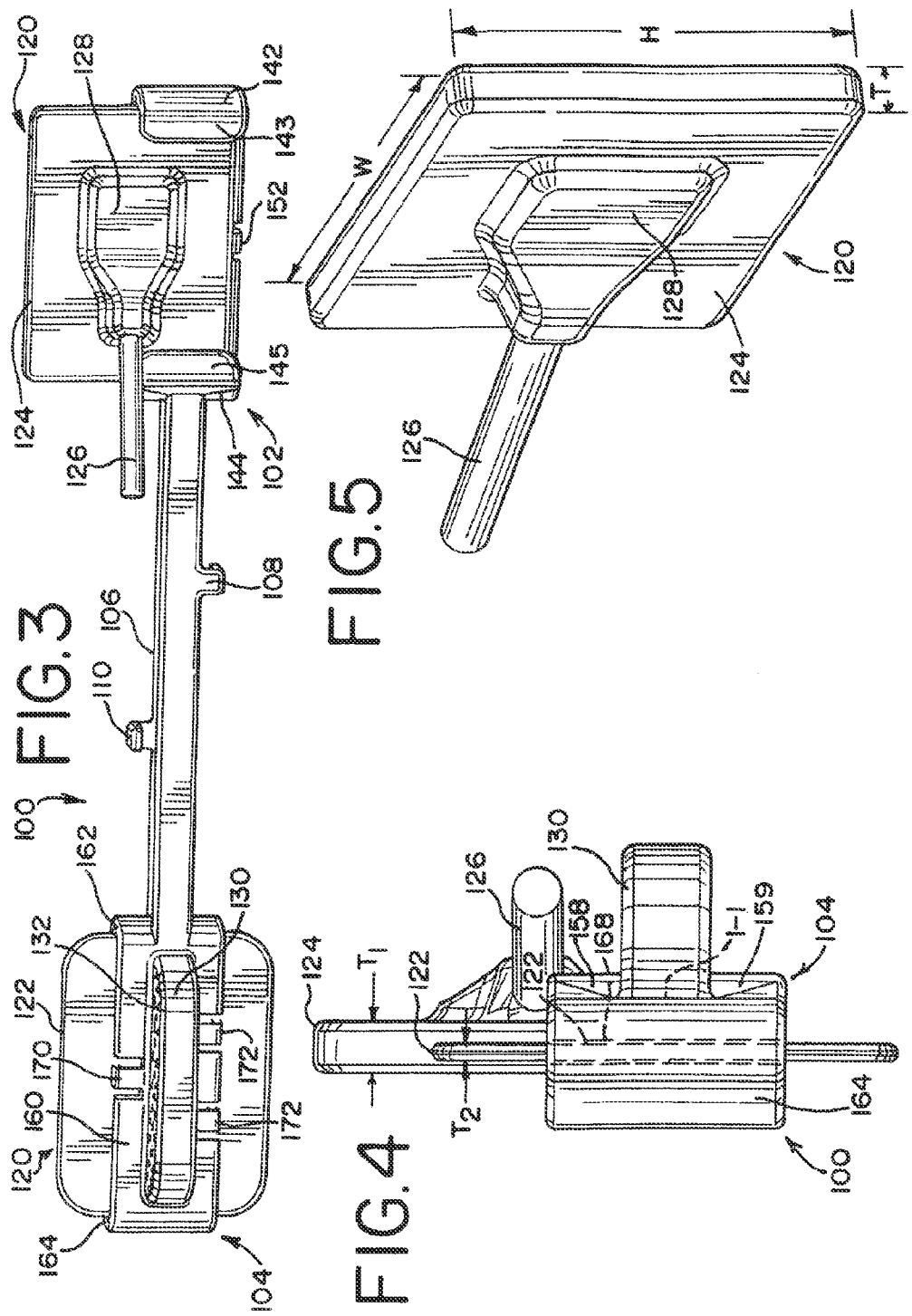

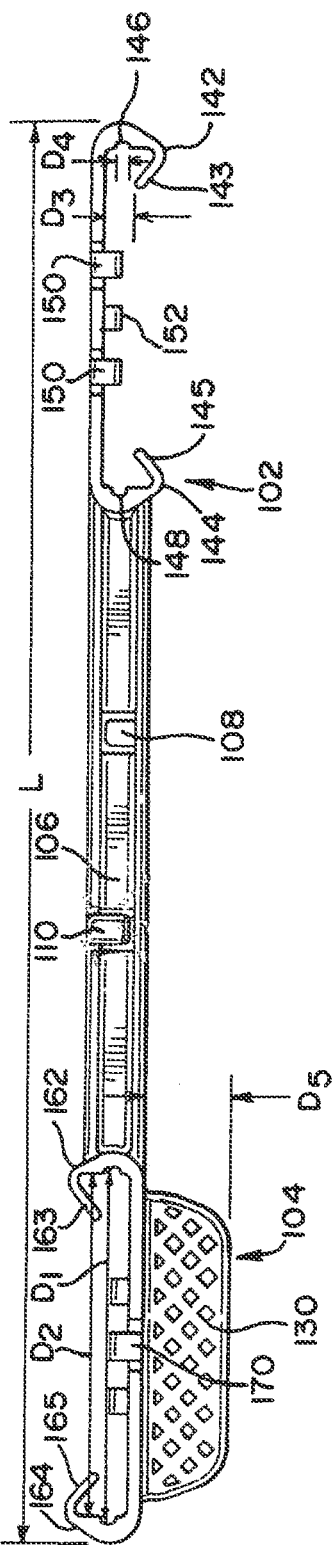
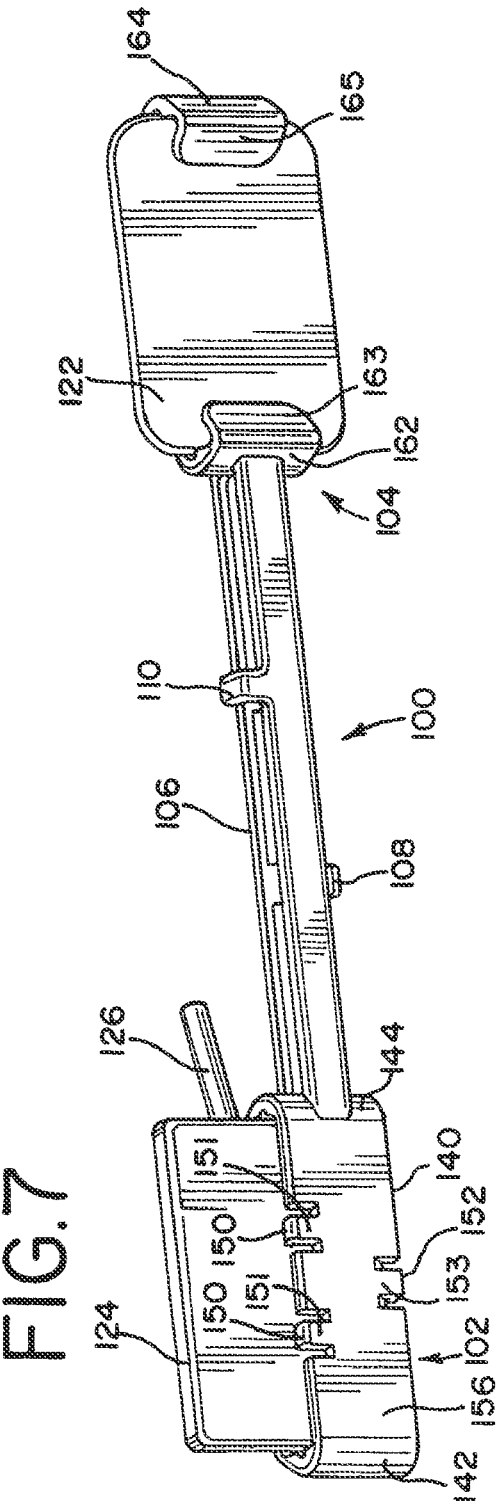

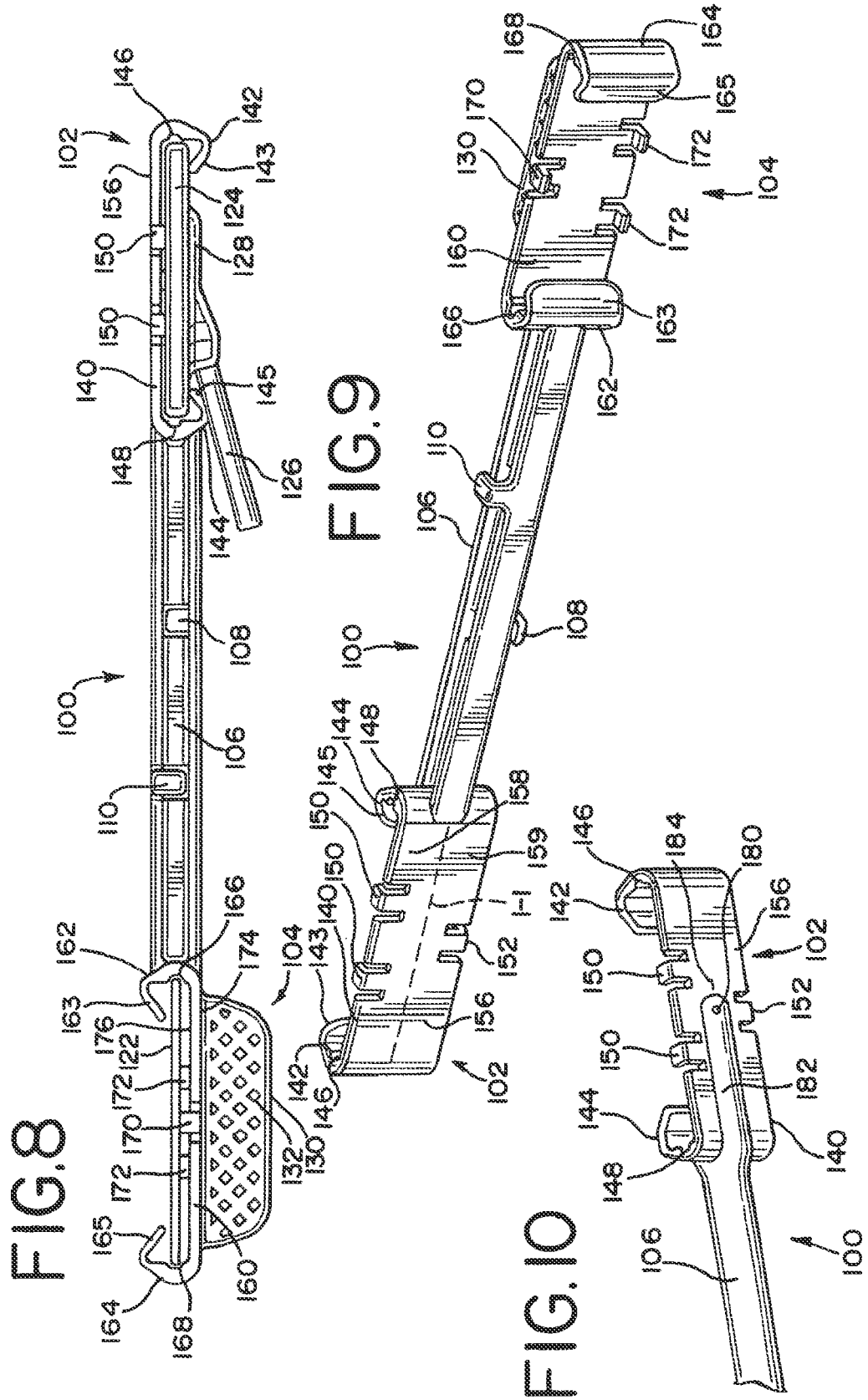

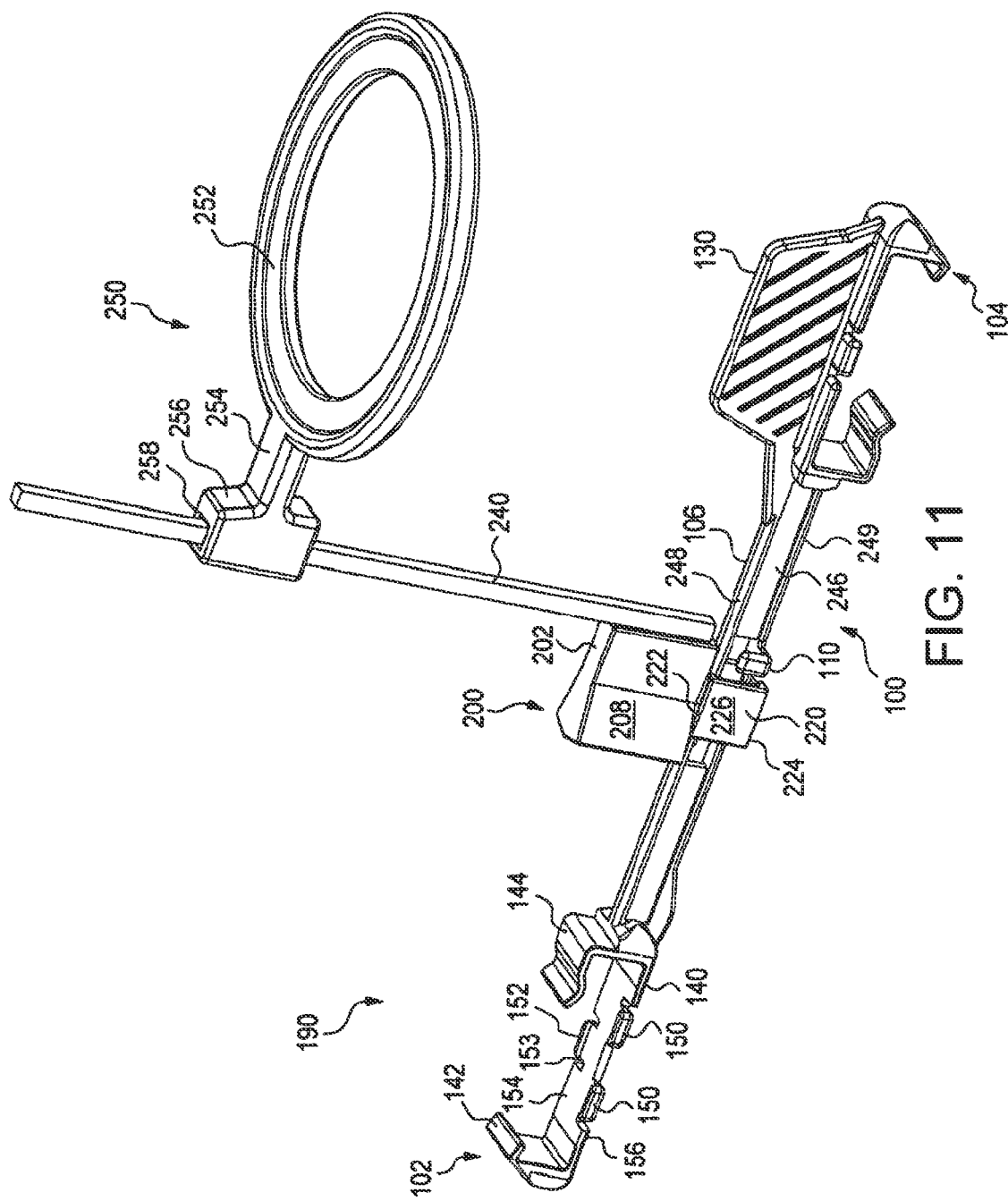

RADIATION SENSING DEVICE AND HOLDER

CROSS REFERENCE TO RELATED APPLICATIONS

The Present Application is a continuation of U.S. patent application Ser. No. 12/345,303, entitled "RADIATION SENSING DEVICE AND HOLDER" and filed Dec. 29, 2008 with the United States Patent and Trademark Office, which is a continuation-in-part of U.S. patent application Ser. No. 11/945,215, entitled "RADIATION SENSING DEVICE AND HOLDER" and filed Nov. 26, 2007 with the United States Patent and Trademark Office, now U.S. Pat. No. 7,819,579, the contents of which are hereby incorporated by reference in their entirety to the extent permitted by law.

BACKGROUND

This invention relates generally to sensor holders, and in particular, to an adapter for connecting a first type of rod and ring to a second type of holder for a dental radiation sensing device.

Dental radiographs are made using x-ray examination units, often including an x-ray cone or tube positioned proximate the patient and aligned to take x-rays of certain teeth. Dental x-ray sensing devices, which include including x-ray film units, digital x-ray sensors, charge coupled devices, phosphor imaging plates or the like, often have a generally flat or plate-like configuration and standardized dimensions so that the sensing device can be placed into the oral cavity.

The sensing device is placed into the patient's mouth and held in place proximate to the tooth or teeth to be examined. The x-ray's are directed through the target teeth and then through the sensor. It has been found that proper orientation of the sensor is required to eliminate distortions and improper focus.

To ensure proper orientation of the sensing device, sensor carriers or holders with "bite blocks" have been developed. These devices often have a plate for holding the sensing device and a bite block that the patient bites down upon to position the device and the carried sensor. A bite block is shown for example, in U.S. Pat. No. 3,473,026.

Different sensing devices are often used depending upon the area of the mouth to be examined. This may include for example, endo, posterior, anterior, left, right, upper and lower bite wings, and the like. Known bite blocks and sensor holders have been individually designed and manufactured for each different type of sensing device. The dimensions of the sensing device and the holder dictate the degree of secured positioning of the sensing device in the holder.

A dental professional may have a large number of x-ray sensing devices with varying sizes and shapes, and hence, a similarly large number of sensor holders. The dental professional is often faced with employing a different sensing device or set of sensing devices, holders and bite blocks depending upon the particular x-ray procedure being employed and the area of the mouth to be examined. At best, it is time consuming to change between sensing devices, sensor holders and bite blocks.

In order to precisely align the x-ray cone or tube with a particular x-ray sensing device held by a particular sensor holder, a rod and ring guide combination may be employed. The rod is typically attached to a particular sensor holder at one end and connected with the ring guide at the other end. The ring guide helps to aim the x-ray cone or tube at the x-ray sensing device. However, some times, in order to take x-rays of various different portions of the mouth, multiple sensor holders may need to be attached to a particular rod and ring guide combination.

A need exists therefore, for adapting a particular sensor holder for use with a particular rod and ring guide combination to take x-rays of various different portions of the mouth.

SUMMARY

The present invention is defined by the following claims, and nothing in this section should be taken as a limitation on those claims. By way of introduction, the preferred embodiments described below relate to a system for holding and aligning a radiation sensing device. The system includes a radiation sensing device having a sensor engagement member. The system also includes a holder having a retention member including first and second retention guides connected with opposing ends of a back plate. The first retention guide also includes a complementary holder engagement member configured to mate with the sensor engagement member at a preset position.

The preferred embodiments also relate to a holder for holding and aligning a radiation sensing device. The holder includes a retention member including a back plate and first and second retention guides connected with opposing ends of the back plate. The first retention guide forms a holder engagement member configured to mate with a complementary sensor engagement member on the radiation sensing device at a preset position.

The preferred embodiments also relate to a radiation sensing device including a housing encasing a digital sensor for sensing radiation and a sensor engagement member connected with the housing for engaging a complementary holder engagement member connected with a holder for holding the radiation sensing device.

DESCRIPTION OF THE DRAWINGS

FIG. 1 depicts a perspective view of a holder for a radiation sensor and/or a radiation film unit, in accordance with one preferred embodiment of the invention.

FIG. 2 depicts an enlarged partial perspective view of a holder for a radiation sensor and/or a radiation film unit holding a radiation sensor, in accordance with one preferred embodiment of the invention.

FIG. 3 depicts an enlarged partial perspective view of a holder for a radiation sensor and/or a radiation film unit holding a radiation film unit, in accordance with one preferred embodiment of the invention.

FIG. 4 depicts side view of a holder for a radiation sensor and/or a radiation film unit holding a radiation sensor, in accordance with one preferred embodiment of the invention.

FIG. 5 depicts a perspective view of a radiation sensor, in accordance with one preferred embodiment of the invention.

FIG. 6 depicts a top view of a holder for a radiation sensor and/or a radiation film unit, in accordance with one preferred embodiment of the invention.

FIG. 7 depicts a perspective view of a holder for a radiation sensor and/or a radiation film unit, in accordance with one preferred embodiment of the invention.

FIG. 8 depicts a top view of a holder for a radiation sensor and/or a radiation film unit, in accordance with one preferred embodiment of the invention.

FIG. 9 depicts a perspective view of a holder for a radiation sensor and/or a radiation film unit, in accordance with one preferred embodiment of the invention.

FIG. 10 depicts a partial perspective view of a holder for a radiation sensor and/or a radiation film unit, in accordance with one preferred embodiment of the invention.

FIG. 11 depicts a first perspective view of a holder for a radiation sensor and/or a radiation film unit connected with a ring guide using a ring guide adapter, in accordance with one preferred embodiment of the invention.

Figure 12:
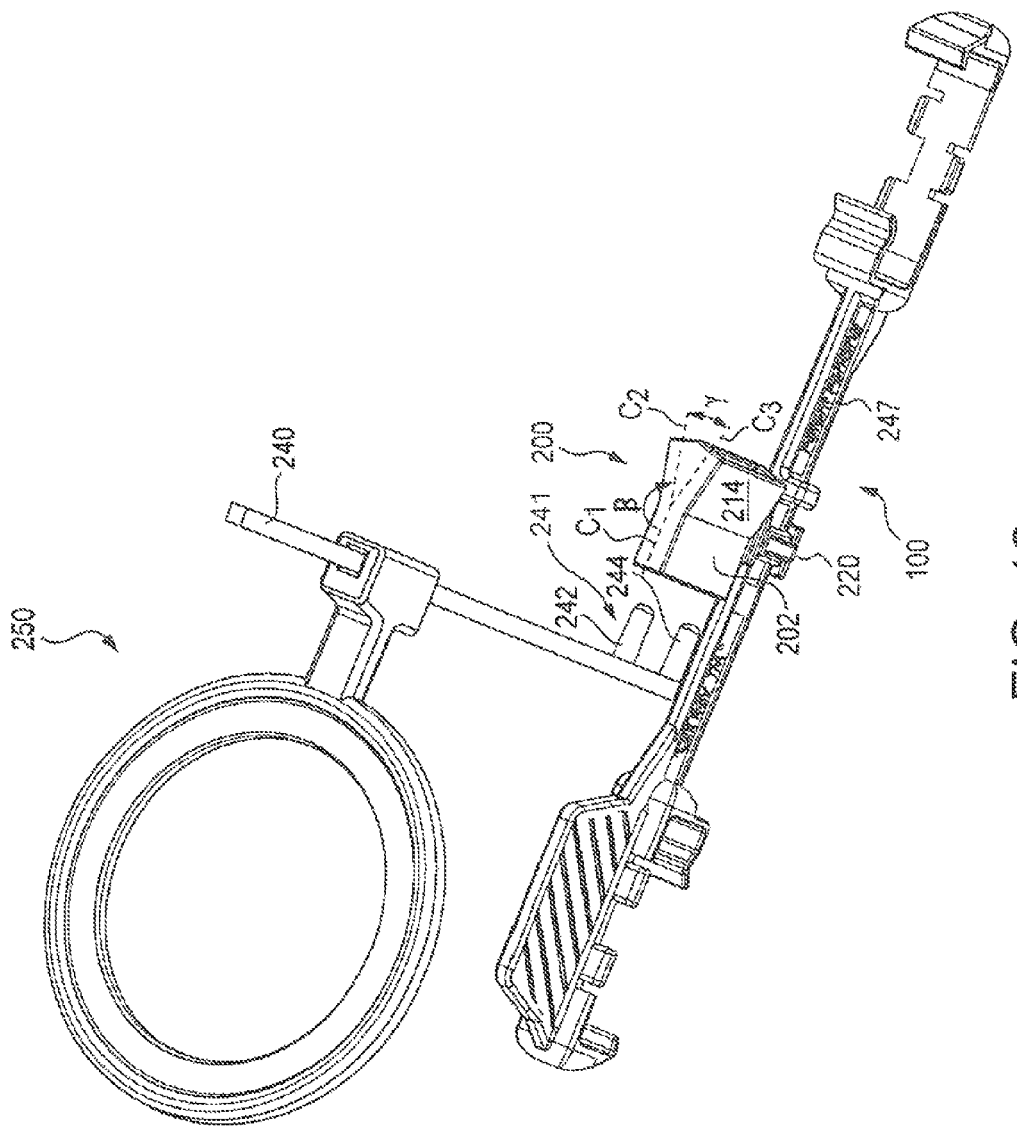
FIG. 12 depicts a perspective view of the ring guide adapter of FIG. 11 being connected with a rod and a ring guide holder at a first alignment member, in accordance with one preferred embodiment of the invention.

It should be appreciated that for simplicity and clarity of illustration, elements shown in the Figures have not necessarily been drawn to scale. For example, the dimensions of some of the elements are exaggerated relative to each other for clarity. Further, where considered appropriate, reference numerals have been repeated among the Figures to indicate corresponding elements.

DETAILED DESCRIPTION

Referring to FIG. 1, there is shown a perspective view of a holder 100 for a radiation sensing device 120, according to one preferred embodiment. The holder 100 is designed to hold and retain the radiation sensing device 120 in a multitude of positions. Preferably, the holder 100 is manufactured using an injection molded process in order to reduce costs. However, holder 100 can be manufactured in one of many ways. For example, holder 100 may be machined, thermoformed, and hand-made. Preferably, in order to reduce costs and maintain rigidity, holder 100 is a one-piece unit which is integrally formed. However, holder 100 may comprise multiple parts which are then assembled and fitted together. Preferably, holder 100 is constructed from a rigid yet somewhat flexible material, such as but not limited to: metals such as iron, steel, stainless steel, aluminum, silver, titanium, and brass; plastics, such as ethylene, vinyl, acetate; acrylics, such as acrylonitrol-butadine-styrene; resins; and polymers such as polycarbonate. The holder 100 may be colored any one of various different colors depending on the size and type of sensors used. For example, the holder may be colored white for a size two x-ray film unit or colored green for a size zero x-ray film unit.

Radiation sensing device 120 is any device which can be used to sense radiation, such as gamma wave radiation, light wave radiation and, preferably, x-ray radiation. As illustrated in FIGS. 1-5, radiation sensing device 120 includes such devices as a radiation film unit 122, which uses film 129 to detect radiation, such as x-ray radiation, a radiation sensor unit 124, which uses a digital sensor 128 or a charge coupled device to detect radiation such as x-rays, a phosphor imaging plate or the like. Radiation sensor unit 124 may include a wire 126 which is used to provide power and/or transfer signals between the digital radiation sensor 128 and a control unit, not shown. Preferably, radiation sensing device 120 is a dental x-ray sensing device which is sized for use in the mouth of a patient in order to take x-ray scans of a patient's teeth.

The holder 100 includes a first retention member 102 and a handle 106 connected with the first retention member 102, as illustrated in FIGS. 1-3. The first retention member 102 includes a back plate 140, a first retention guide 142, and a second retention guide 144, as illustrated in FIGS. 1, 7, and 9. The first retention guide 142 is connected with an end of the back plate 140 and the second retention guide is connected with an opposing end of the back plate 140. The first retention guide 142 faces the second retention guide 144. Preferably, the back plate 140, the first retention guide 142, and the second retention guide 144 are integrally formed, as shown in FIGS. 1, 7, and 9. Preferably, each retention guide 142, 144 forms a generally u-shaped cross section.

More preferably, each retention guide 142, 144 forms a generally u-shaped cross section having a gripping portion 143, 145, respectively, wherein each gripping portion 143, 145 curves inwards towards the back plate 140, as illustrated in FIGS. 1, 6, 8, and 9. The gripping portions 143, 145 help to better hold the radiation sensing device 120 in place and allow the holder 100 to accommodate a wide variety of radiation sensing devices with varying thicknesses, such as both radiation film units 122 and radiation sensor units 124, as illustrated in FIGS. 1 and 8, or such as radiation sensor units of varying thicknesses. Preferably, the gripping portions 143, 145 are apply enough pressure on the radiation sensing device 120 to hold the device 120 in place without damaging the device 120. With this configuration, holder 100 can receive the radiation sensing device 120, by sliding the radiation sensing device 120 in between the first retention guide 142 and the second retention guide 144 and against the back plate 140, as illustrated in FIGS. 1-3.

Preferably the retention guides 142, 144 are sized such that radiation sensing device 120 fits firmly between the first retention guide 142 and the second retention guide 144 and against the back plate 140, as illustrated in FIGS. 1, 2, 8, and 9. Preferably each retention guide 142, 144 extends from an upper portion of the back plate 140 to a lower portion of the back plate 140, as illustrated in FIGS. 4 and 9. As defined herein, an upper portion of the back plate 140 is a portion of the back plate 140 that is within an upper half 158 of the back plate 140 and a lower portion of the back plate 140 is a portion of the back plate 140 that is within a lower half 159 of the back plate 140. Dividing the back plate 140 into two halves, wherein each half extends from the first retention guide 142 to the second retention guide 144, one half is the upper half 158 and the opposing half is the lower half 159, as illustrated in FIGS. 4 and 9, wherein the back plate 140 is divided into halves by imaginary line 1-1 located centrally in back plate 140.

In one embodiment the first retention member 102 includes a retention stop, such as an upper retention stop 150, on a front surface 154 of the back plate 140. The retention stop is preferably between the retention guides 142, 144, as illustrated in FIGS. 6-9. Preferably the first retention member 102 comprises an upper retention stop 150 connected with an upper portion of the back plate 140, and a lower retention stop 152 opposed to the upper retention stop 150 and connected with a lower portion of the back plate 140. Preferably both the upper and lower retention stops, 150, 152 are located between the retention guides 142, 144. The retention stops 150, 152 include a portion which extends away from the back plate 140 and allow for a user to position the radiation sensing device 120 either towards the bottom portion of the back plate 140, or towards the upper portion of the back plate 140, as illustrated in FIGS. 2 and 7. By allowing a user to change the position of the radiation sensing device 120 in this way, the holder 100 allows a user to position the radiation sensing device 120 more accurately when radiation is applied to either the upper or lower teeth in a patient's mouth. Preferably, each retention stop 150, 152 extends in a direction from the first retention guide 142 to the second retention guide 144, as illustrated in FIG. 7.

Preferably, the first retention member 102 includes flexible members 151, 153 attached to each retention stop 150, 152, respectively, at one end and attached to the back plate 140 at a second end, as illustrated in FIG. 7. The flexible members 151, 153 may be formed in the back plate 140, or may be formed on the back plate 140, and allow the retention stops 150, 152 to move back and forth upon insertion of a radiation sensing device 120 into the first retention member 102. Additionally, by allowing the retention stops 150, 152 to move back and forth, the flexible members 151, 153 also allow the retention stops 150, 152 to apply an appropriate amount of pressure on the radiation sensing device 120, such that the radiation sensing device 120 is held in place yet not damaged. In one embodiment, the first retention member 102 includes more than one upper retention stop 150, as illustrated in FIG. 7. The additional retention stop 150 allows for better placement of the radiation sensing device 120.

In one embodiment, each retention guide 142, 144 forms a retention groove 146, 148 for receiving a radiation film unit 122, as illustrated in FIGS. 1, 4, and 6, and 8. The retention grooves 146, 148 forms a u-shape cross section which is smaller than the u-shaped cross section formed by each retention guide 142, 144. By forming a smaller u-shaped cross section, the retention grooves 146, 148 are better able to receive a radiation film unit 122, since generally, the radiation film unit 122 has a smaller thickness $T_2$ than a thickness $T_1$ of the radiation sensor unit 124, as illustrated in FIG. 1. In this manner by using retention grooves 146 and 148, a single retention member 102, 104 is able to accommodate both a radiation film unit 122 and a radiation sensing device 120, as illustrated in FIGS. 1 and 8.

In one embodiment, the holder 100 includes a first wire retention member 108 on the handle 106, as illustrated in FIG. 1. Wire retention member 108 is able to accommodate and grasp a wire such as the wire 126 found in radiation sensor unit 124. Preferably, the handle 106 also includes a groove 113 in which wire can reside in. Working in conjunction with wire retention member 108, groove 113 is able to accommodate and secure a wire such as the wire 126 found in radiation sensor unit 124, therefore preventing the wire from becoming tangled within a user's mouth. Preferably, the wire retention member 108 is formed on the handle 106 adjacent the first retention member 102.

In one embodiment, the holder 100 includes a second wire retention member 110 on the handle 106, as illustrated in FIG. 1. Wire retention member 110 is able to accommodate and grasp a wire such as the wire 126 found in radiation sensor unit 124. Preferably, the handle 106 also includes a groove 111 in which wire can reside in. Working in conjunction with wire retention member 110, groove 111 is able to accommodate and secure a wire such as the wire 126 found in radiation sensor unit 124, therefore preventing the wire from becoming tangled within a user's mouth. Preferably, the wire retention member 110 is formed on the handle 106 adjacent a second retention member 104.

In one embodiment, the holder 100 includes a second retention member 104 connected with the handle 106, wherein the second retention member 104 is opposed to the first retention member 102. The second retention member 104 functions essentially the same way as the first retention member 102 and may include many of the same elements as found in the first retention member 102. In one embodiment, the second retention member 104 includes a back plate 160, retention guides 162, 164, gripping portions 163, 165, retention grooves 166, 168, an upper retention stop 170, and a lower retention stop 172, as illustrated in FIGS. 1, 3, and 6-9. Preferably, the first retention member 102 is connected with one end of the handle 106 and the second retention member 104 is connected with an opposing end of the handle 106 as illustrated in FIG. 1. Preferably, the first and second retention members 102, 104 are each sized differently so that each retention member 102, 104 can accept a radiation sensing device 120 of a different size. For example, in one embodiment the first retention member 102 may be sized to accept a first radiation sensing device 120 and a second retention member 104 may be sized to accept a second radiation sensing device 120, wherein the size of the first radiation sensing device 120 is not equal to the size of the second radiation sensing device 120.

In one embodiment, the holder 100 comprises a bite block 130 on a back surface 174 of the back plate 160, wherein the back surface 174 opposes a front surface 176, as illustrated in FIGS. 1 and 8. The bite block 130 is preferably positioned centrally on the back plate between the upper retention slot 170 and lower retention slot 172 as illustrated in FIG. 3. When the holder 100 is inserted into a patient's mouth, the patient is able to bite down with the patient's teeth on the bite block 130 and engage the first retention member 102. The bite block 130 allows for more accurate positioning of the holder 100, and more specifically the first retention member 102 and the sensor 120, within a patient's mouth. Preferably, the bite block 130 includes a series of serrations 132, as illustrated in FIGS. 1 and 6, in order to provide additional grip and less movement for the holder 100 within the patient's mouth. Preferably, the serrations 132 are diamond shaped and are indented into the bite block.

As illustrated in FIG. 6, the length L from one end of the holder 100 to another end of the holder 100 in a direction from a first retention member to a second retention member 104, is approximately between 5 and 50 centimeters and more preferably between 10 and 30 centimeters and most preferably between 15 and 25 centimeters. Additionally, the distance $D_1$ between a first retention groove 146 and a second retention groove 148 is preferably between 3 and 8 centimeters. Additionally, a distance $D_2$ between a first retention guide 142 and a second retention guide 144, as illustrated in FIG. 6, is preferably between 3 and 8 centimeters. A distance $D_3$ between the back plate 140 and a far end of a retention guide 142, 144, as illustrated in FIG. 6, is preferably between 1 and 20 millimeters, and more preferably, between 2 to 10 millimeters, and a distance $D_4$ between one end of the retention groove and a second end of the retention groove, as illustrated in FIG. 6, is approximately between 0.1 and 4 millimeters, and more preferably, between 0.5 and 3 millimeters. A distance $D_5$ from the back surface of the back plate 140 to a distal surface of the bite block 130, as illustrated in FIG. 6, is preferably between 1 and 3 centimeters.

Radiation sensing devices 120 can vary in width W, height H and thickness T as illustrated in FIG. 5. Preferably the width W of the radiation sensing device 120 is between 3 and 8 centimeters. Also preferably the height H of the radiation sensing device 120 is between 1 and 4 centimeters and the thickness T is preferably between 0.1 and 20 millimeters, and more preferably, between 1 to 10 millimeters.

In one embodiment, the holder 100 includes a pivoting member 182 attached to the back plate 140 of the first retention member 102 at a pivot point 180 and connected with the handle 106, as illustrated in FIG. 10. The pivoting member 182 allows the first retention member 102 to be pivoted at the pivot point 180, thus providing the holder 100 with the ability to rotate the retention member 102 at a variety of angles with respect to the handle 106. The pivoting member 182 also provides the user with a variety of configurations in which the holder may be placed, and therefore provides the user with additional flexibility when positioning the holder 100, and more specifically, the retention member 102. Preferably, the back plate 140 includes a series of stops 184 projecting radially outwards from the pivot point 180. The stops 184 may either be in the form of grooves formed in the back surface 156 or in the form of projections formed on the back surface 156. The stops 184 engage the pivoting member 182 and stop the pivoting member 182 from pivoting at preselected angles with respect to the handle 106, as illustrated in FIG. 10.

In one embodiment, a system 190 for holding and aligning a radiation sensing device 120 is provided, as shown in FIG. 11. The system 190 includes the holder 100 for the radiation sensing device 120, a ring guide adapter 200 removably connected with the holder 100, a rod 240 removably connected with the ring guide adapter 200, and a ring guide 250 which is slidably connected with the rod 240.

Figure 13:
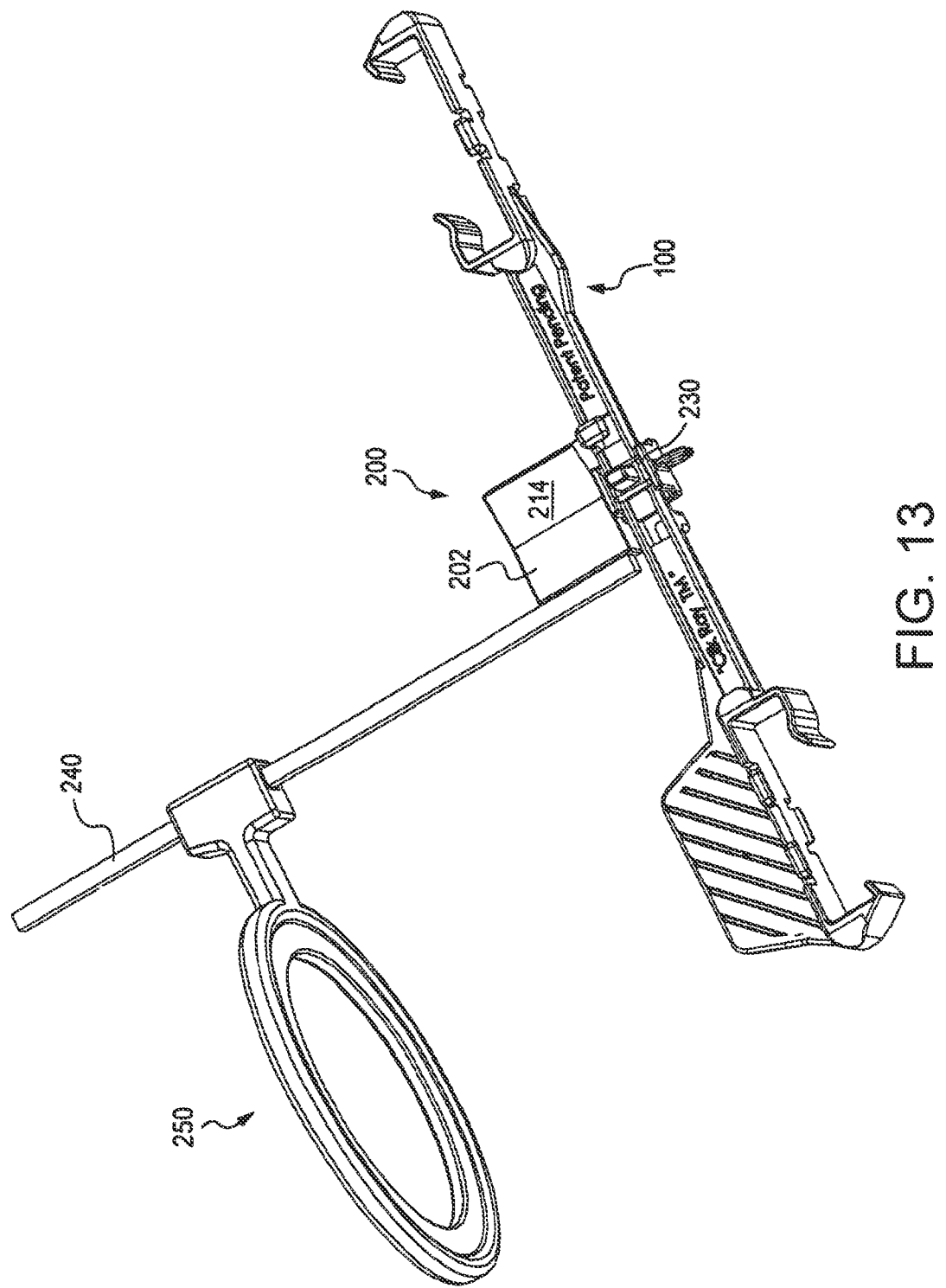
FIG. 13 depicts a second perspective view of a holder for a radiation sensor and/or a radiation film unit connected with a ring guide using a ring guide adapter, in accordance with one preferred embodiment of the invention.
Figure 20:
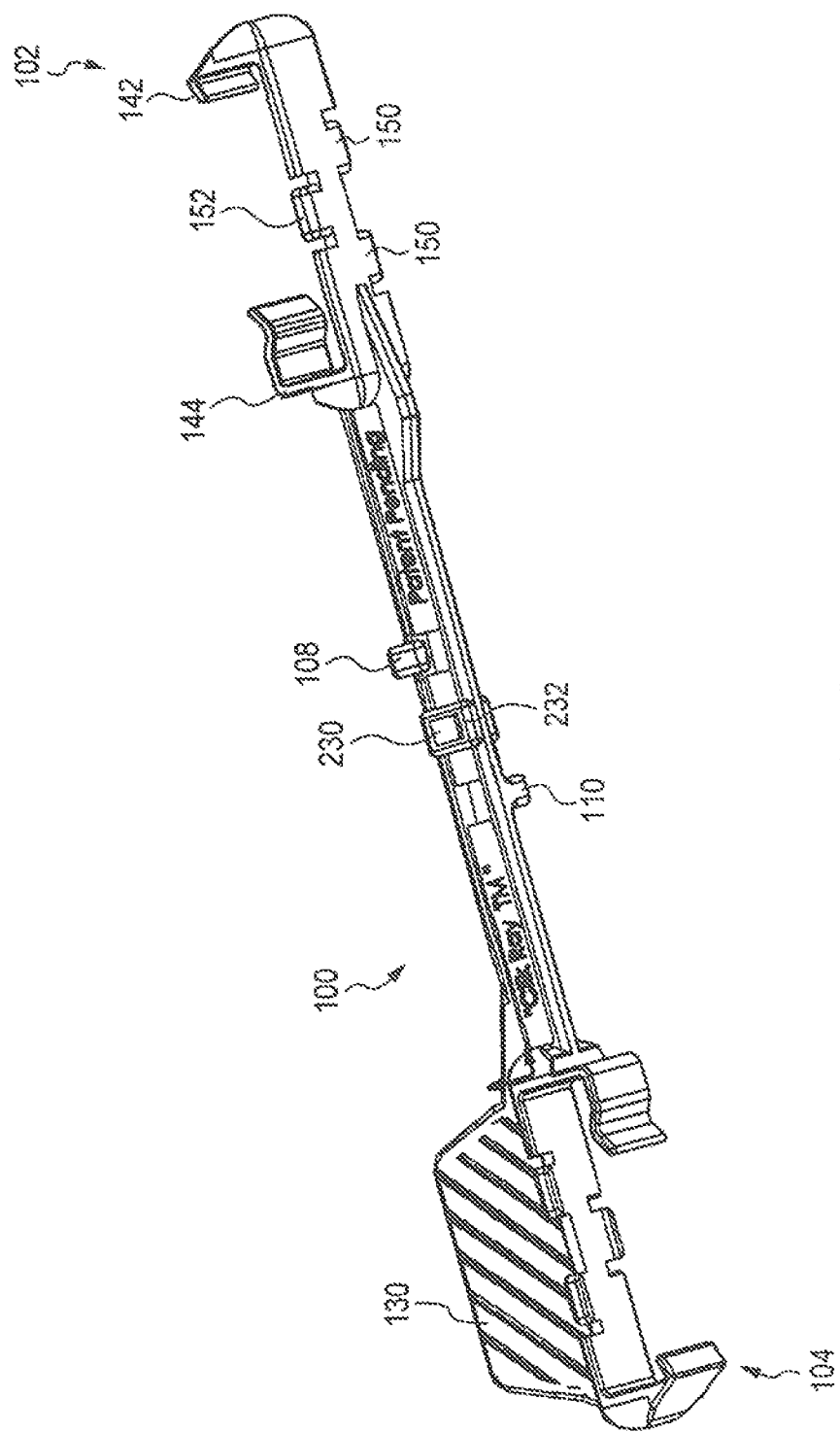
FIG. 20 depicts an enlarged perspective view of the holder for a radiation sensor and/or a radiation film unit of FIG. 11, in accordance with one preferred embodiment of the invention.

While in this embodiment, the system 190 includes the holder 100, any device which can hold a radiation sensing device 120 can be used in substitution for the holder 100, such as U.S. Pat. Nos. 2,239,569, 2, 240,336, 4,484,342, 4,489, 427, 4,965,885, 5,090,047, 5, 677, 537, and 6,461,038. The holder 100 includes at least one retention member 102 for holding a radiation sensing device 120 and a handle 106 connected with the retention member 102, as shown in FIG. 20. In this embodiment, the holder 100 also includes an engagement member 230. As used herein, an engagement member, such as the engagement member 230, may be any device which is adapted to removably connect with another device, and includes such thing as: mechanical fasters including hook and loop type fasters such as VELCRO™, projecting members such as keys, channels and cavities such as key-holes, snap-fit arrangements, a frictional arrangement which includes members which frictionally engage each other, screws, nails, nuts and bolts, hydraulic engagement; chemical fasteners such as epoxy or other types of glue, solder or other types of welding engagements; magneto-electrical fasteners such as magnets, electrical magnets, and charged couplings. Preferably, the engagement member 230 is a channel 232 which goes into or through the handle 106, as shown in FIG. 20. The engagement member connects with and mates with a complementary engagement member 220 of the ring guide adapter 200, as shown in FIGS. 11-13.

Figure 15:
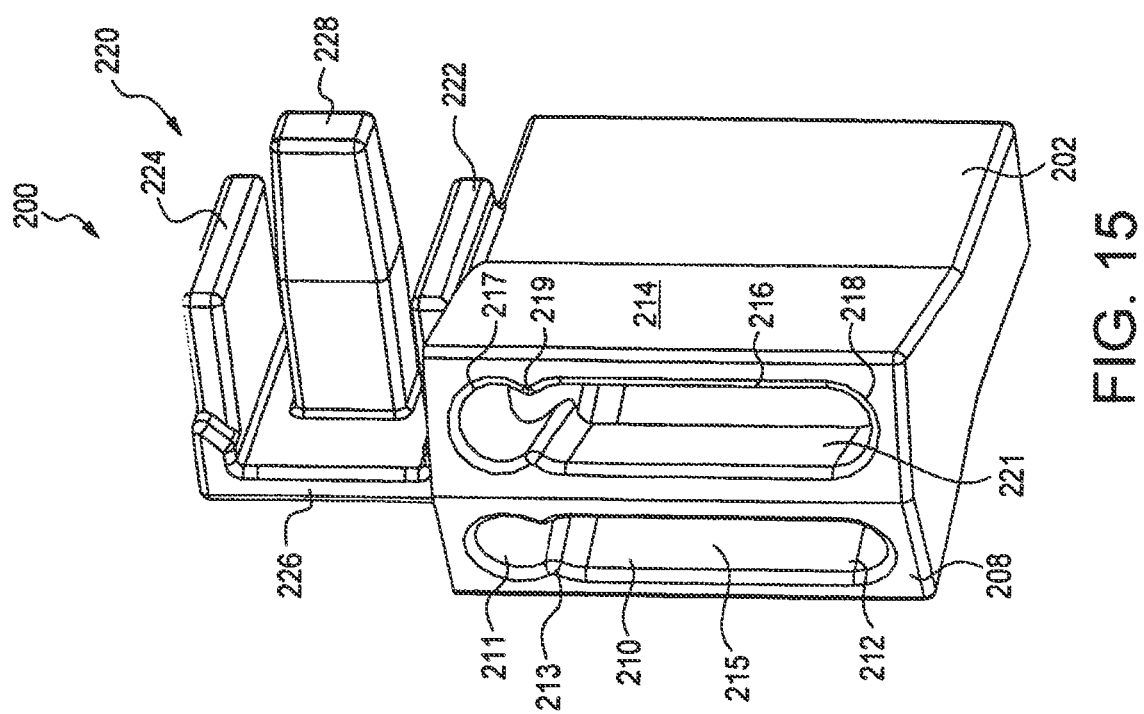
FIG. 15 depicts an enlarged first perspective view of the ring guide adapter of FIG. 11, in accordance with one preferred embodiment of the invention.
Figure 16:
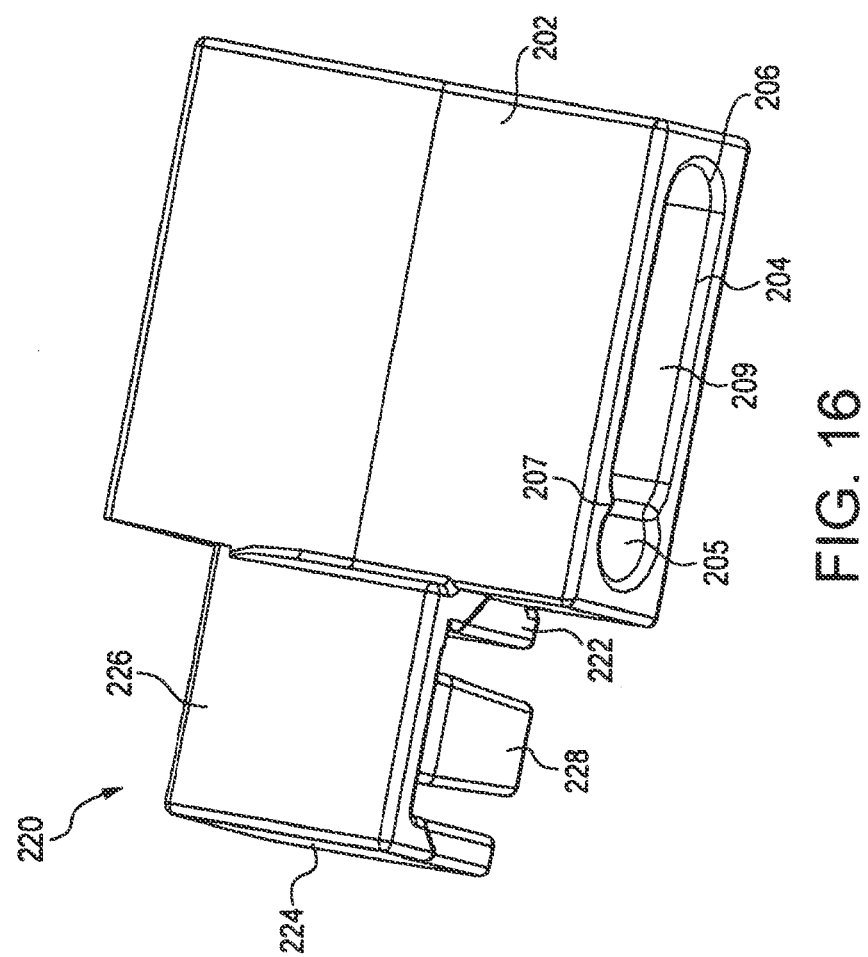
FIG. 16 depicts an enlarged second perspective view of the ring guide adapter of FIG. 11, in accordance with one preferred embodiment of the invention.
Figure 17:
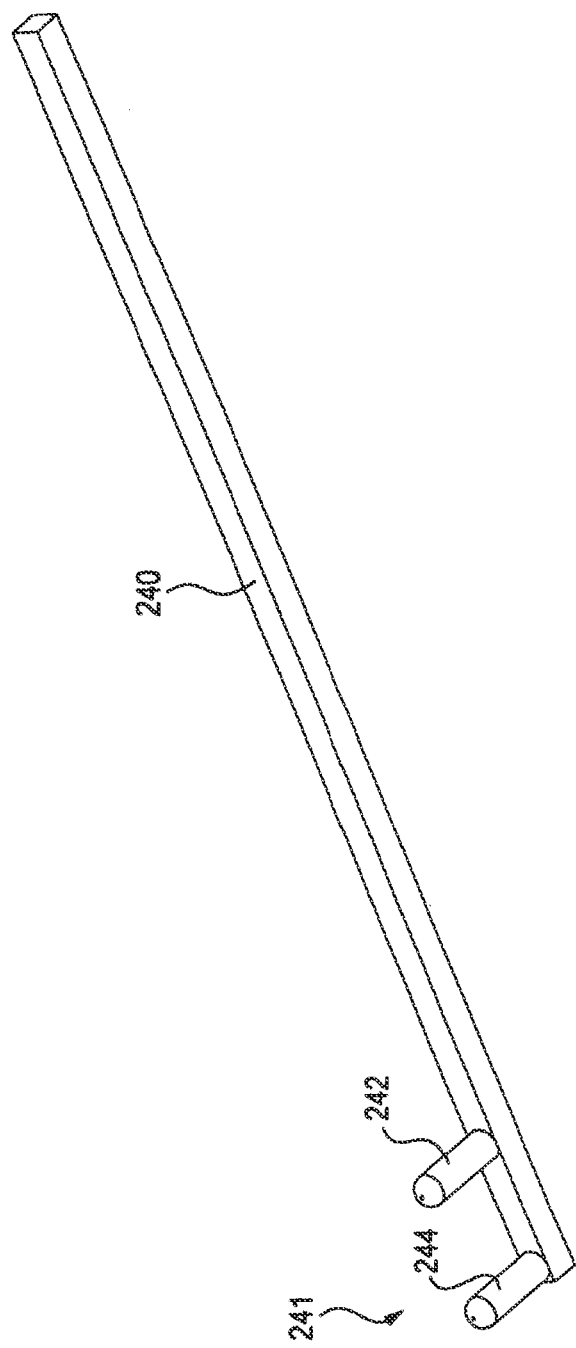
FIG. 17 depicts an enlarged perspective view of the rod of FIG. 12, in accordance with one preferred embodiment of the invention.

The ring guide adapter 200 includes first, second and third alignment members 202, 208, 214. Each alignment member 202, 208, 214 includes an engagement member 204, 210, 216, respectively, which is removably connected with and mates with a complementary engagement member 241 on the rod 240, as shown in FIGS. 12 and 17. Preferably, the engagement members 204, 210, 216 are cavities 209, 215, 221 which are formed in each respective engagement member 204, 210, 216. Preferably, the cavities 209, 215, 221 receiving a pair of projections 242, 244 of the engagement member 241. In order to insure a snug fit, in one embodiment, the cavities 209, 215, 221 are formed in the shape of a key-hole and include semi-circular upper portions 205, 211, 217 which are connected with generally U-shaped lower portions 206, 212, 218 through a pair of bends 207, 213, 219, respectively, as shown in FIGS. 15 and 16.

Rod 240 connects the ring guide 250 with the handle 106 through the use of the adapter 200. Preferably, the rod 240 is composed of a rigid material such as a metal like aluminum, steel, or nickel. The rod 240 allows the ring guide 250 to be positioned a distance away from either the first or second retention member 102, 104. Preferably, the rod 240 is slidably connected with the ring guide 250 through a channel 258 which is formed through a connecting portion 254 of the ring guide 250, as shown in FIG. 11. This allows the distance between the ring guide 250 and either the first or second retention member 102, 104 to be varied.

The rod 240 is removably connected with either the first, second or third alignment members 202, 208, 214 of the ring guide adapter 200. More specifically, the rod 240 includes engagement member 241, which is preferably positioned at one end of the rod 240, and which mates with one of the engagement members 204, 210, 216 on the adapter 200, as discussed above. The rod 240 preferably has a multi-sided cross section, such as a square cross-section, to prevent the ring guide 250 from rotating on the rod 240 and to provide precise alignment between the first or second retention member 102, 104 and the ring guide 250. The rod 240 and the ring guide 250 can be any standard or known arrangement of rods and ring guides and includes such devices as those shown in U.S. Pat. No. 3,473,026; the XCP Film Holding System manufactured by Dentsply Rinn™ of Elgin, Ill.; and the RAPD Positioning System™ manufactured by Flow X-Ray Corporation of Deer Park, N.Y.

The ring guide 250 is used to precisely aim a radiation generating machine, such as an x-ray machine, at and direct radiation from the radiation generating machine to either retention member 102, 104. The ring guide 250 includes a guide 256 which is slidably connected with the rod 240, a ring 252, and a connecting portion 254 connecting the ring 252 to the guide 256, as shown in FIGS. 11-14. The guide 256 forms a channel 258 through which the rod 240 is positioned. In this manner, the rod 240 is slidably engaged with and connected with the ring guide 250. The ring 252 is a generally circular member which is used to aim and align a cone of a radiation generating machine with either retention member 102, 104, so that radiation emitted from the machine are precisely directed towards the radiation sensing device 120 situated in either retention member 102, 104.

Figure 14:
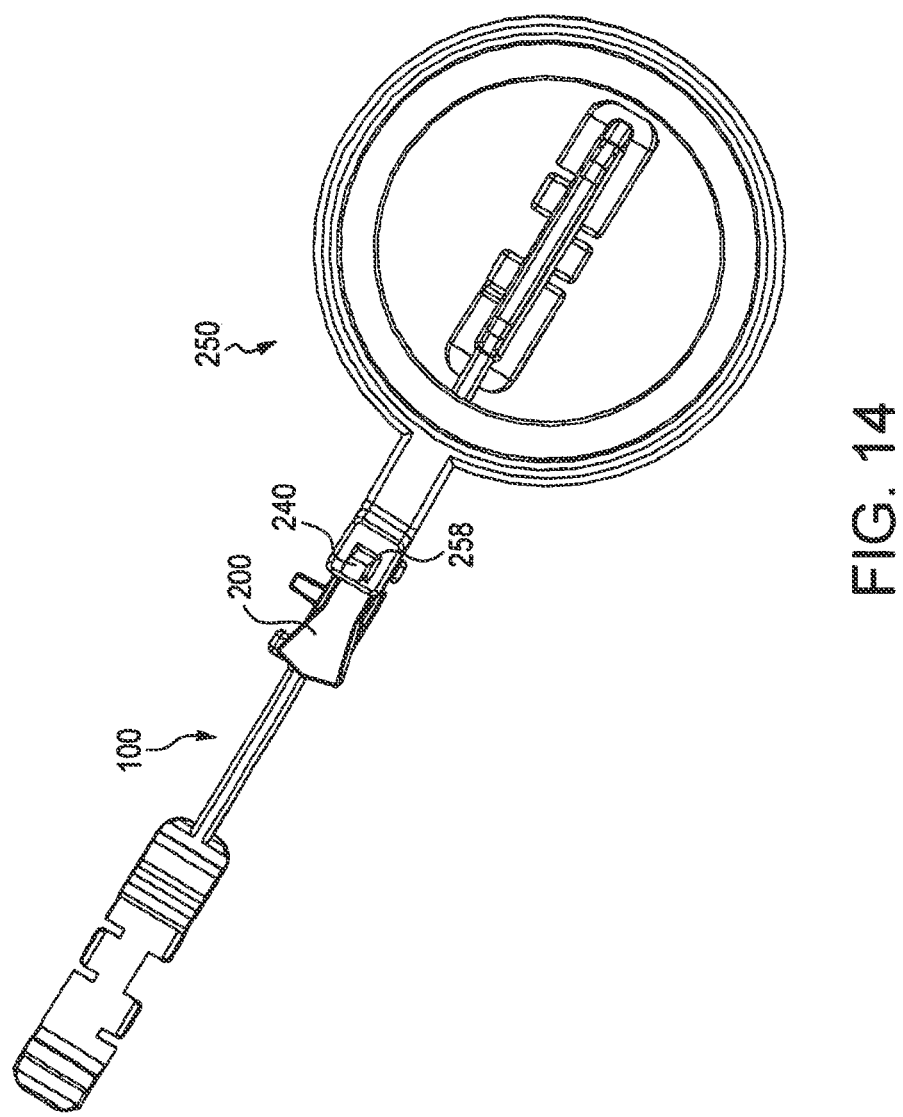
FIG. 14 depicts a side view of the holder for a radiation sensor and/or a radiation film unit connected with the ring guide in a first position using the ring guide adapter of FIG. 11, in accordance with one preferred embodiment of the invention.
Figure 18:
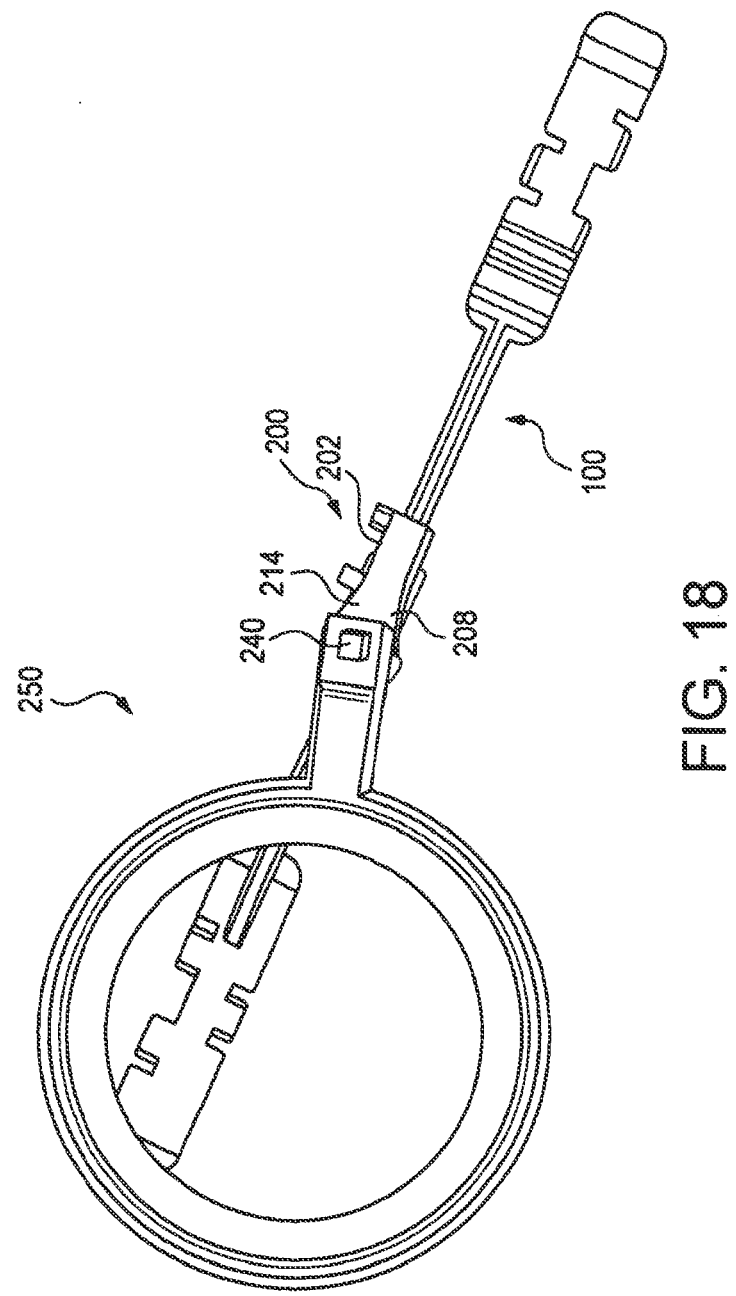
FIG. 18 depicts a side view of the holder for a radiation sensor and/or a radiation film unit connected with the ring guide in a second position using the ring guide adapter of FIG. 11, in accordance with one preferred embodiment of the invention.
Figure 19:
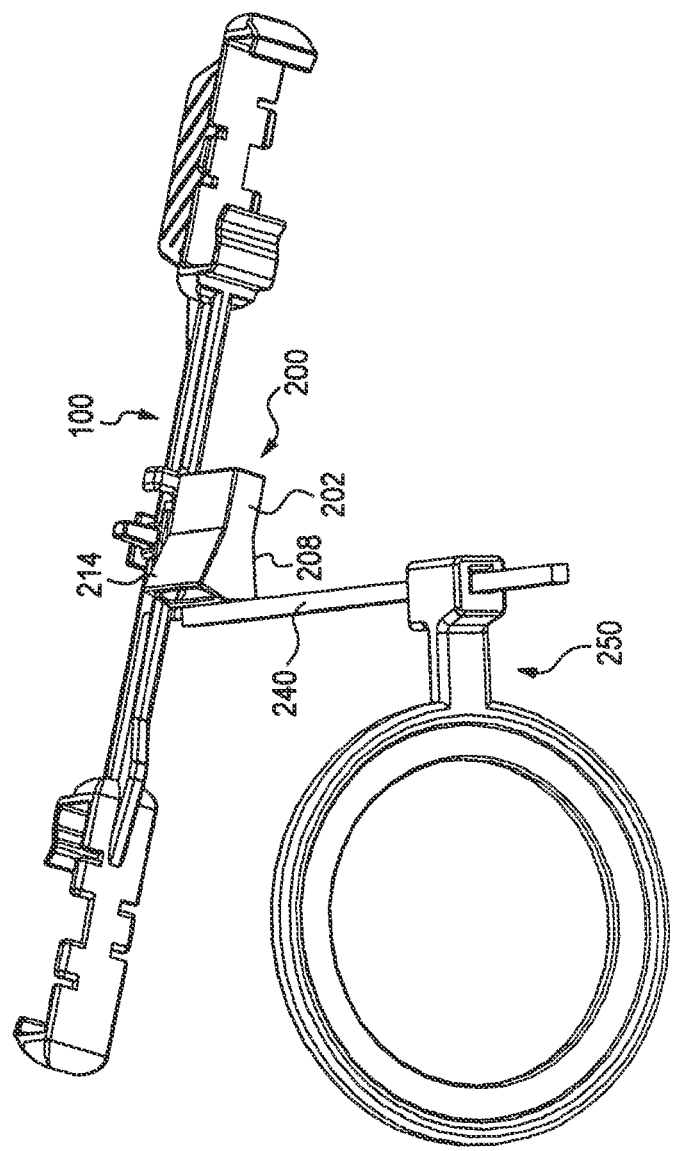
FIG. 19 depicts a perspective view of the holder for a radiation sensor and/or a radiation film unit connected with the ring guide in a second position using the ring guide adapter of FIG. 11, in accordance with one preferred embodiment of the invention.
Figure 21:
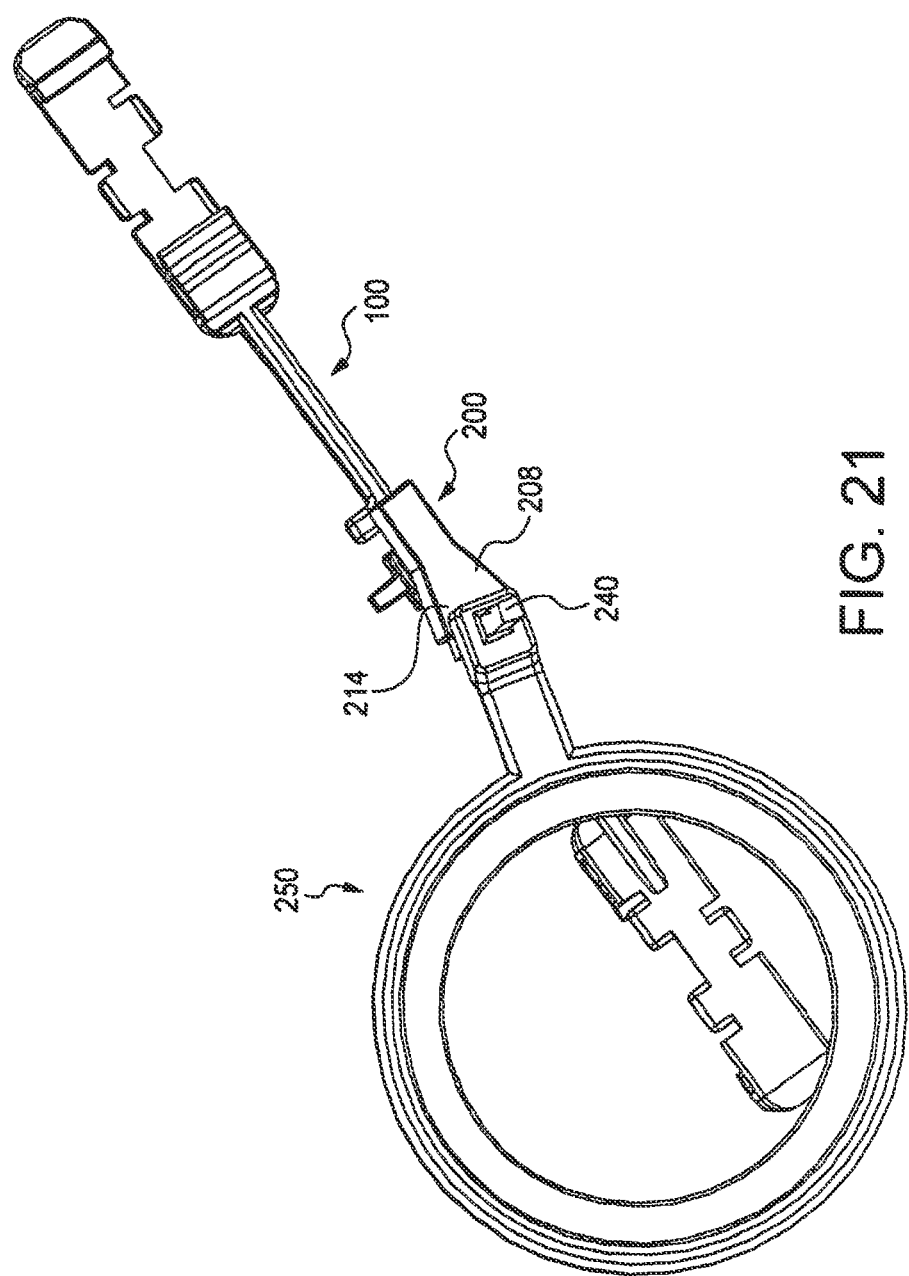
FIG. 21 depicts a side view of the holder for a radiation sensor and/or a radiation film unit connected with the ring guide in a third position using the ring guide adapter of FIG. 11, in accordance with one preferred embodiment of the invention.
Figure 22:
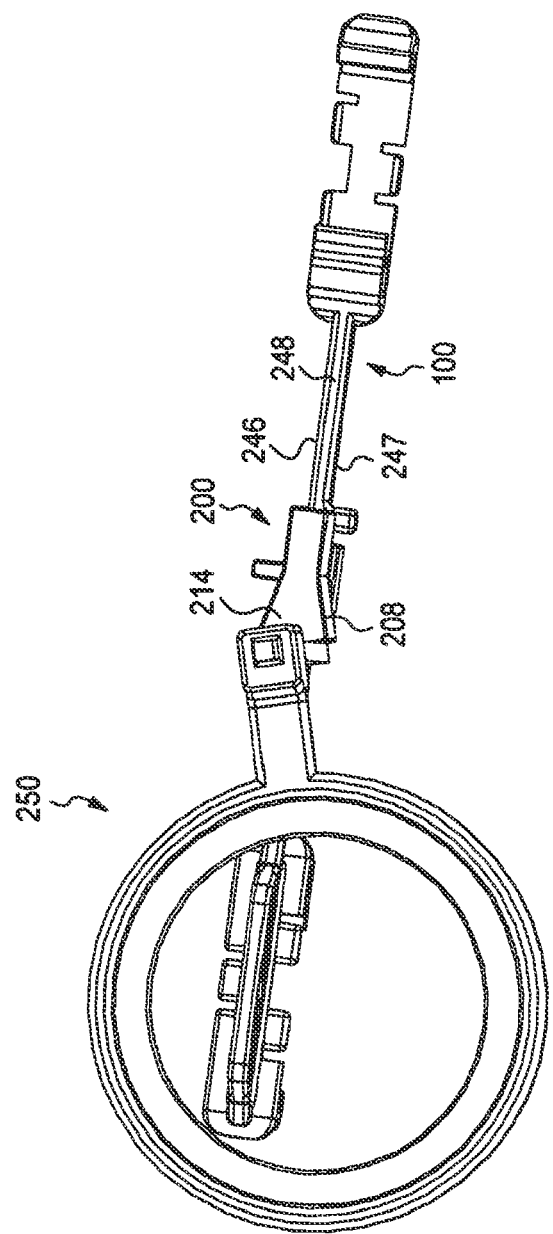
FIG. 22 depicts a side view of the holder for a radiation sensor and/or a radiation film unit connected with the ring guide in a fourth position using the ring guide adapter of FIG. 11, in accordance with one preferred embodiment of the invention.
Figure 23:
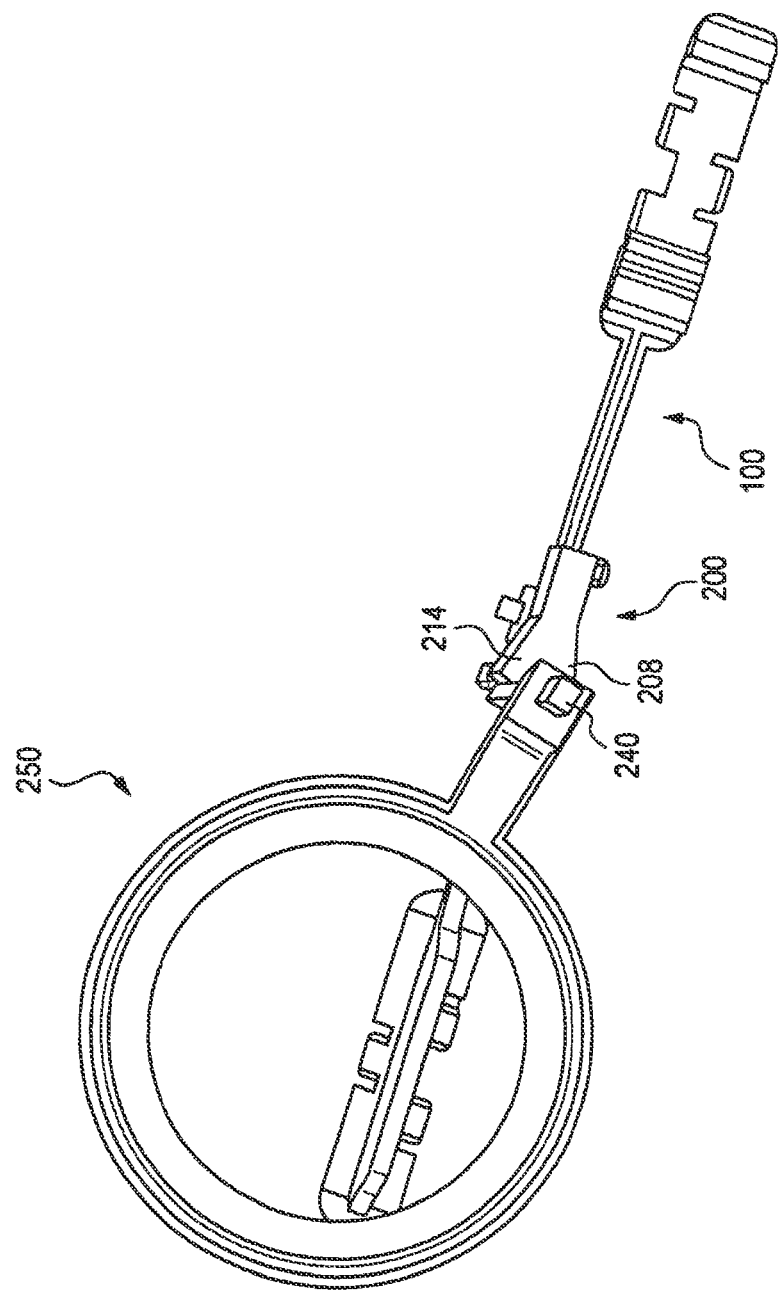
FIG. 23 depicts a side view of the holder for a radiation sensor and/or a radiation film unit connected with the ring guide in a fifth position using the ring guide adapter of FIG. 11, in accordance with one preferred embodiment of the invention.

There are three basic positions to place the ring 252 in with respect to either retention member 102, 104 for taking three basic types of radiographs: 1) a central position in which the ring 252 is aimed at the center of either retention member 102, 104 for taking bite wing or anterior type radiographs, as shown in FIG. 14, a lower position in which the ring 252 is aimed at the a lower portion of either retention member 102, 104 for taking lower posterior type radiographs, as shown in FIGS. 18, 19 and 22; and an upper position, which is opposite the lower position, in which the ring 252 is aimed at an upper portion of either retention member 102, 104 for taking upper posterior type radiographs, as shown in FIGS. 21 and 23. Preferably, the first, second, and third alignment members 202, 208, 214 are positioned on the ring guide adapter 200 so that when the rod 240 is removably connected with the first alignment member 202, the ring guide 250 is positioned for a first radiograph type, such as a bite wing or anterior type radiograph; so that when rod 240 is removably connected with the second alignment member 208, the ring guide 250 is positioned for a second radiograph type, such as a lower posterior type radiograph; and so that when rod 240 is removably connected with the third alignment member 214, the ring guide 250 is positioned for a third radiograph type, such as a upper posterior type radiograph.

Preferably, the ring guide adapter 200 is removably connected with the engagement member 230 of the holder 100 through a complementary engagement member 220. Preferably, the engagement member 220 is a frictional arrangement which includes a lower plate 222 connected with an upper plate 224 through a connecting plate 226, and includes a projecting member 228 which is connected with and extends away from a surface of the connecting plate 226 and between the lower and upper plates 222, 224, as shown in FIGS. 15 and 16. When connecting the engagement member 220 of the adapter 200 with the engagement member 230 of the holder 100, the projecting member 228 is inserted into and through the channel 232, as shown in FIGS. 12 and 13. Additionally, lower, upper, and connecting plates 222, 224, 226 partially surround and engage lower, upper, and left or right sides 249, 248, 246, 247 of the handle 106 of the holder 100, as shown in FIGS. 11-13. In this manner, the ring guide adapter 200 is able to be removably connected with the holder 100. Preferably, the channel 232 and the projecting member 228 are designed in such a way so that the projecting member 228 can be inserted in at least one of two different ways.

For example, in one embodiment, the projecting member 228 has a rectangular cross section which mates with a rectangular cross section of the channel 232 in one of four ways. In a first way, the projecting member 228 is inserted into the channel 232 so that the lower plate 222 engages the upper side 248, the upper plate 224 engages the lower side 249, and the connecting plate 226 engages the left side 246 of the holder 106, as shown in FIG. 11. This arrangement allows the ring guide 250 to align with a central portion of the second retention member 104 by mating the rod 240 with a first alignment member 202 of the ring guide adapter 200 in order to take central bite wing or anterior type radiographs which are positioned to capture portions of both the upper and lower teeth of a person's mouth. In a second way, the projecting member 228 is inserted into the channel 232 so that the lower plate 222 engages the upper side 248, the upper plate 224 engages the lower side 249, and the connecting plate 226 engages the right side 247 of the holder 106, as shown in FIGS. 22 and 23. This arrangement allows the ring guide 250 to align with either an lower or upper portion of the second retention member 104 by mating the rod 240 with either a second or third alignment member 208, 214 of the ring guide adapter 200 in order to take, respectively, either lower posterior radiographs which are positioned to mainly capture portions of the lower teeth of a person's mouth, or upper posterior radiographs which are positioned to mainly capture portions of the upper teeth of a person's mouth.

In a third way, the projecting member 228 is inserted into the channel 232 so that the lower plate 222 engages the lower side 249, the upper plate 224 engages the upper side 248, and the connecting plate 226 engages the left side 246 of the holder 106. This arrangement allows the ring guide 250 to align with a central portion of the first retention member 102 by mating the rod 240 with the first alignment member 202 of the ring guide adapter 200 in order to take central bite wing or anterior type radiographs which are positioned to capture portions of both the upper and lower teeth of a person's mouth. In a fourth way, the projecting member 228 is inserted into the channel 232 so that the lower plate 222 engages the lower side 249, the upper plate 224 engages the upper side 248, and the connecting plate 226 engages the right side 247 of the holder 106, as shown in FIGS. 18, 19 and 21. This arrangement allows the ring guide 250 to align with either a lower or upper portion of the first retention member 102 by mating the rod 240 with either the second or third alignment member 208, 214 of the ring guide adapter 200 in order to take, respectively, either lower posterior radiographs which are positioned to mainly capture portions of the lower teeth of a person's mouth, or upper posterior radiographs which are positioned to mainly capture portions of the upper teeth of a person's mouth.

In one embodiment, the first, second, and third alignment members 202, 208, 214 are position in a Y-shaped arrangement, as shown in FIG. 12. In this arrangement, the first alignment member 202 is opposed to the second and third alignment members 208, 214. Wherein the first alignment member 202 is aligned along a first centerline $C_1$, the second alignment member 208 is aligned along a second centerline $C_2$, and the third alignment member 214 is aligned along a third centerline $C_3$. An angle α is formed between the second and third alignment members 208, 214, and more specifically between the second and third centerlines $C_2$, $C_3$. Preferably, the angle α is chosen so as to precisely position the ring guide 250 for second and third radiograph types. An angle β is formed between the first and second alignment members 202, 208, and more specifically between the first and second centerlines $C_1$, $C_2$. Preferably, the angle β is chosen so as to precisely position the ring guide 250 for first and second radiograph types. Preferably, the angle α is between 5 and 90 degrees, and more preferably between 10 and 50 degrees, and most preferably about 30 degrees. Preferably, the angle β is between 100 and 180 degrees, and more preferably between 120 and 170 degrees, and most preferably about 165 degrees.

Figure 24:
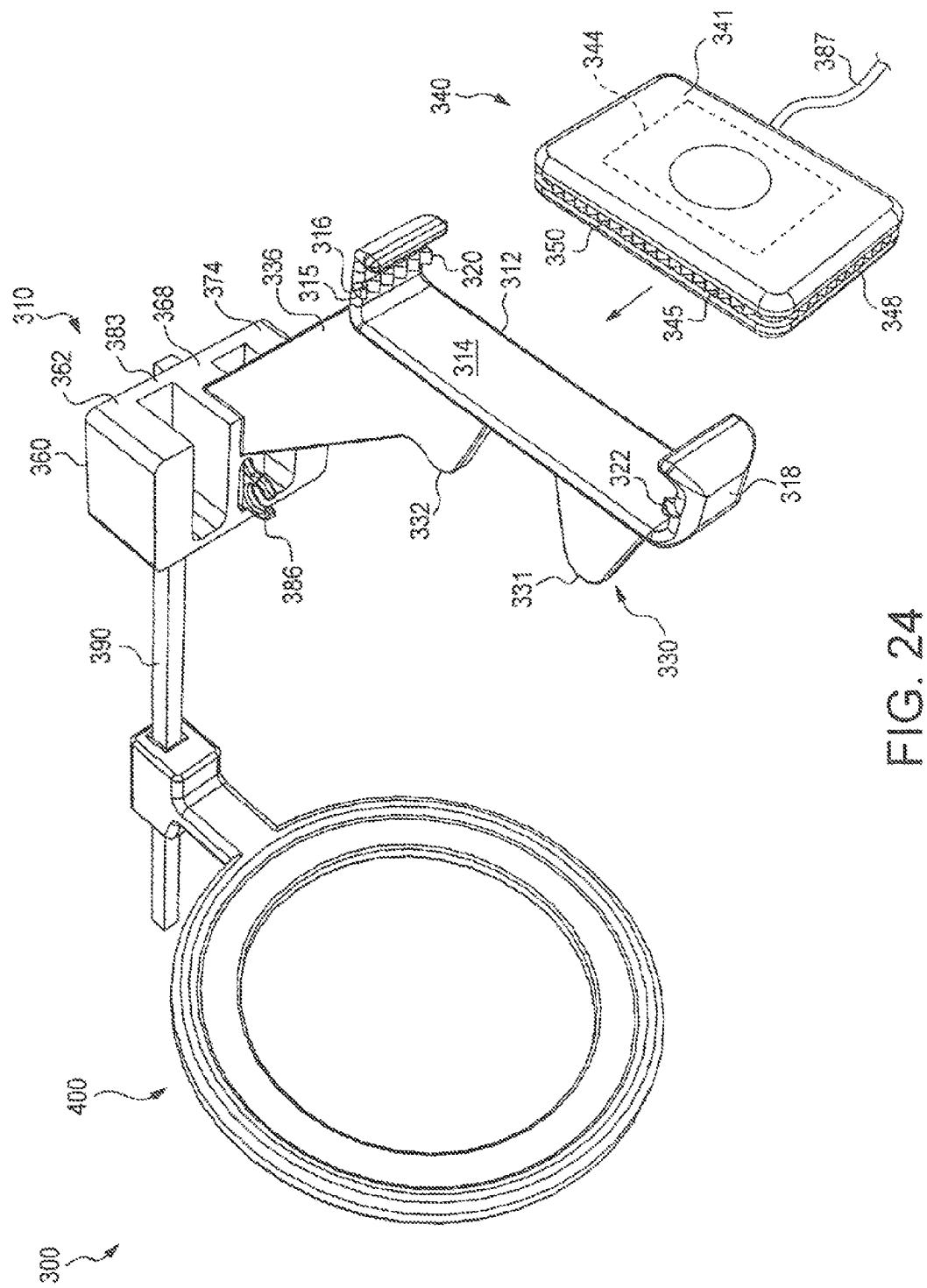
FIG. 24 depicts a perspective view of a radiation sensing device being inserted into a holder connected with a ring guide through a ring guide adapter, in accordance with one preferred embodiment of the invention.

In one embodiment, a second system 300 for holding and aligning a radiation sensing device 340 is provided, as shown in FIG. 24. The system 300 includes a radiation sensing device 340 and a holder 310 for securing and holding the radiation sensing device 340 in a variety of preset positions. The radiation sensing device 340 is any device which can be used to sense radiation, such as gamma wave radiation, light wave radiation and, preferably, x-ray radiation. As illustrated in FIGS. 24-27, radiation sensing device 340 includes such devices as a radiation film unit, which uses film to detect radiation, or a radiation sensor unit 344 which uses a digital sensor, a charge coupled device, or a phosphor imaging plate to detect radiation. Radiation sensing device 340 may include a wire 387 which is used to provide power and/or transfer signals between the radiation sensor unit 344 and a control unit, not shown. Preferably, radiation sensing device 340 is sized for use in the mouth of a patient in order to take x-ray scans of a patient's teeth.

The holder 310 includes at least one retention member 312 for holding the radiation sensing device 340 and a handle 336 connected with the retention member 312, as shown in FIG. 24. The handle 336 is integrally formed with a bite wing 330 which includes a first portion 331 connected with the retention member 312 at a first location and a second portion 332 which is connected with the retention member 312 at a second location and integrally formed with the handle 336, as shown in FIG. 24. The split bite wing 330 allows for less material to be used when forming the holder 310 and the bite wing 330. Additionally, the split bite wing 330 also allows for the use of endodontic files during a procedure when the bite wing 330 is in a patient's mouth. Additionally, integrating the handle 336 with the bite wing 330 also allows for less material to be used when forming the holder 310.

The retention member 312 includes a back plate 314, a first retention guide 316, and a second retention guide 318, as illustrated in FIGS. 24-27. The back plate 314 connects the first retention guide 316 with the second retention guide 318.

While the back plate 314 is shown as being a plate in FIG. 24, the back plate 314 can take on other shapes, such as a rod or paid or rods, so long as the back plate 314 connects the first retention guide 316 with the second retention guide 318. Preferably, the handle 310 and the bite wing 330 are connected with one side of the back plate 314. The first retention guide 316 is connected with an end of the back plate 314 and the second retention guide 318 is connected with an opposing end of the back plate 314. The first retention guide 316 faces the second retention guide 318. Preferably, the back plate 314, the first retention guide 316, and the second retention guide 318 are integrally formed, as shown in FIG. 24. Preferably, each retention guide 316, 318 forms a generally u-shaped cross section so as to better grip the radiation sensing device 340.

Figure 25:
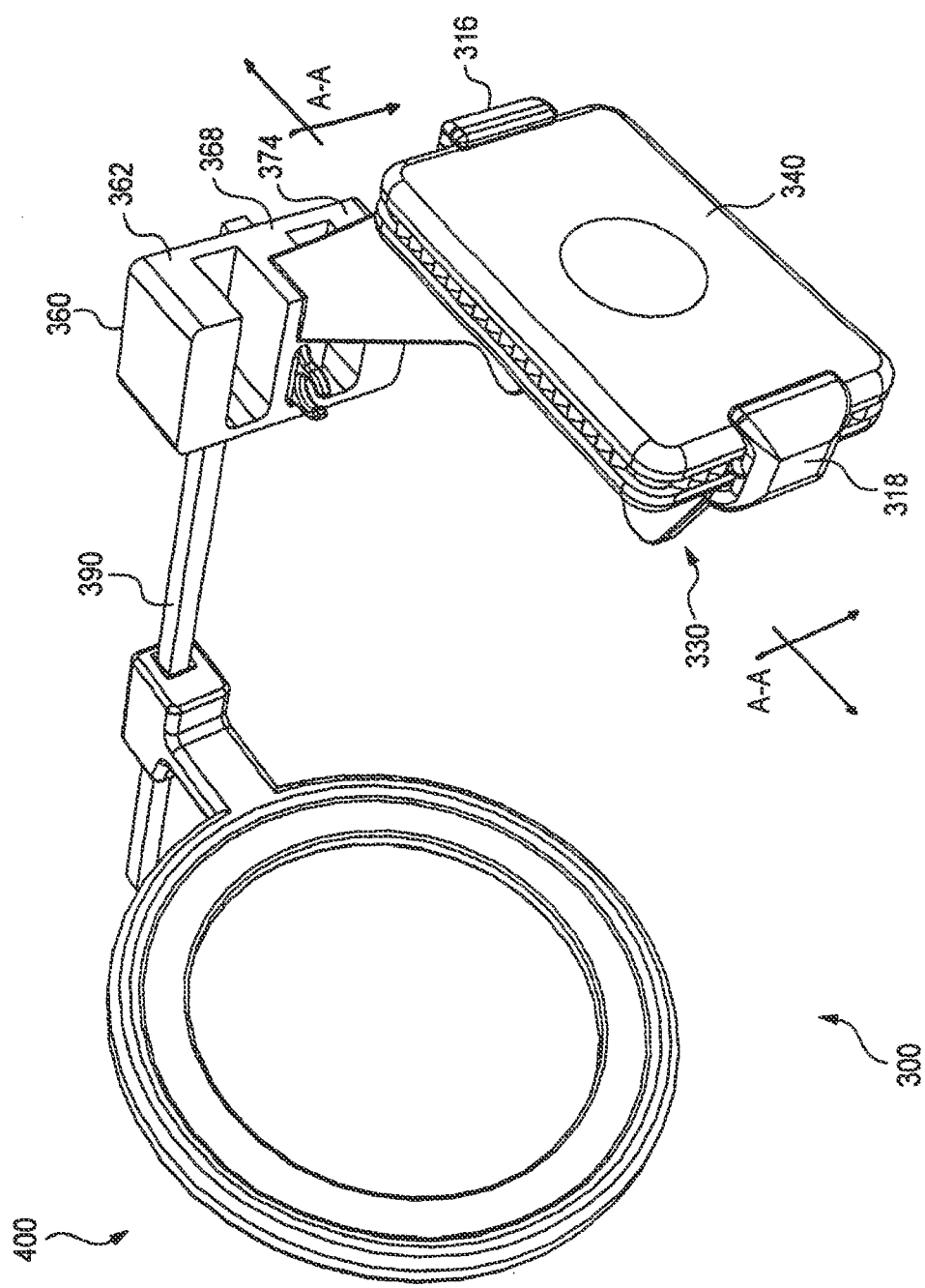
FIG. 25 depicts a perspective view of the radiation sensing device of FIG. 24 inserted into the holder of FIG. 24, in accordance with one preferred embodiment of the invention.
Figure 26:
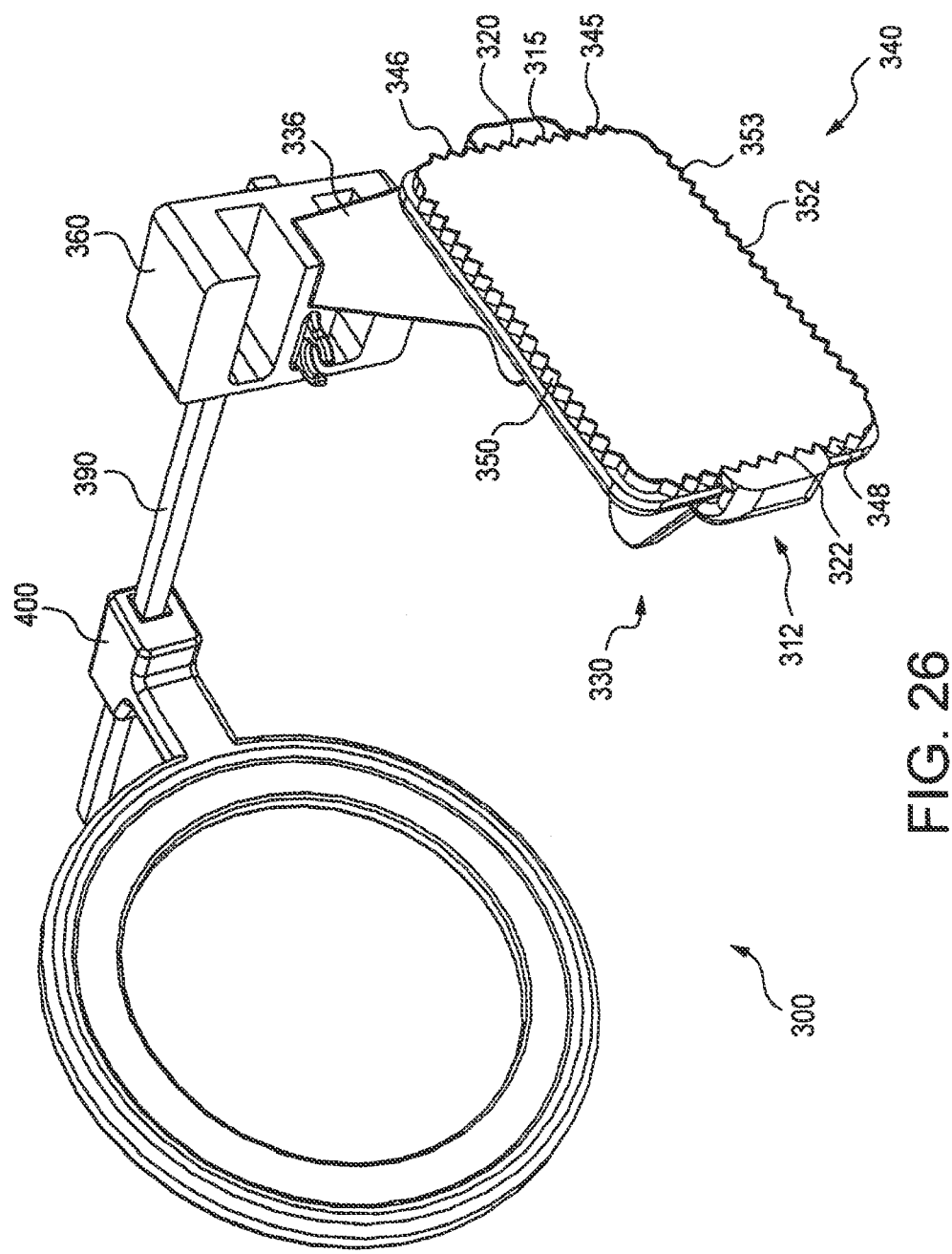
FIG. 26 depicts a cross sectional view of the radiation sensing device and holder of FIG. 25 along plane A-A, in accordance with one preferred embodiment of the invention.
Figure 27:
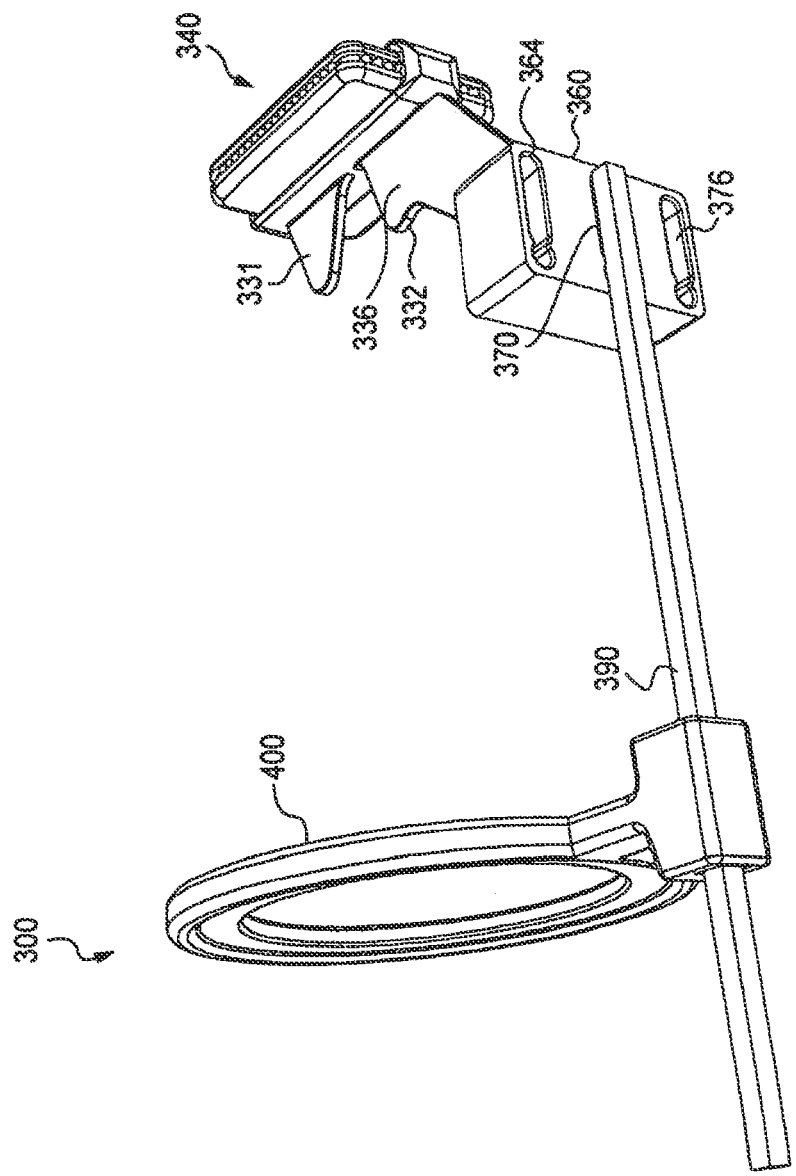
FIG. 27 depicts a second perspective view of the radiation sensing device and holder of FIG. 25, in accordance with one preferred embodiment of the invention.

More preferably, each retention guide 316, 318 forms a generally u-shaped cross section surrounding a holder engagement member 320, 322, respectively, as illustrated in FIGS. 24-26. The engagement members 320, 322 help to better hold the radiation sensing device 340 in place. Preferably the retention guides 316, 318 are sized such that radiation sensing device 340 fits firmly between the first retention guide 316 and the second retention guide 318 and against the back plate 314, as illustrated in FIG. 27. Preferably each retention guide 316, 318 extends in a direction from an upper portion of the back plate 314 to a lower portion of the back plate 314, as illustrated in FIGS. 24-27. With this configuration, holder 310 can receive the radiation sensing device 340, by sliding the radiation sensing device 340 in between the first retention guide 316 and the second retention guide 318 and against the back plate 314, as illustrated in FIGS. 24-27.

Radiation sensing device 340 includes a sensor engagement member 345 connected with either the radiation film unit or the radiation sensor unit 344. Preferably, the sensor engagement member 345 includes an engagement member which is capable of being engaged with a complementary holder engagement member 315 located on the holder 310. As used herein a complementary engagement member mates with and completes an opposing engagement member, such as the sensor engagement member 345. Preferably, the complementary holder engagement member 315 inhibits but does not prevent the opposing engagement member 345 from sliding against the complimentary engagement member 315. Preferably, the complementary engagement member 315 inhibits the opposing engagement member 345 from sliding against the complimentary engagement member 315 at a preset position. The preset position is a predetermined position at which the sensor engagement member 345 and the complimentary holder engagement member 315 mate and lock. The preset position is predetermined based on the geometries of the sensor engagement member 345 and the complimentary holder engagement member 315. For example, in one embodiment the sensor engagement member 345 and the complimentary holder engagement member 315 each form a pair of hills and a valley between the hills, and a preset position is formed when a hill from the sensor engagement member 345 is placed in the valley of the complimentary holder engagement member 315. Preferably, the geometries of the sensor engagement member 345 and the complimentary holder engagement member 315 can form more than one preset position. The preset position helps to lock the sensor in a predetermined and fixed position which helps in aligning the radiation sensing device 340.

As illustrated in FIG. 26, while movement is inhibited between engagement members 315 and 345, movement is not prevented and the two engagement members 315 and 345 can slide against each other and lock at more than one preset position. In one embodiment, the complementary holder engagement member 315 mirrors the opposing sensor engagement member 345, as shown in FIG. 26 through a cross-section of engagement members 315 and 345. In one embodiment, the complimentary holder engagement member 315 includes indentations and protrusions which mate with indentations and protrusions in the opposing sensor engagement member 345, as shown in FIG. 26 through a cross-section of engagement members 315 and 345. Preferably, the complementary holder engagement member 315 does not completely prevent the opposing sensor engagement member 345 from sliding against the complimentary holder engagement member 315.

Figure 28:
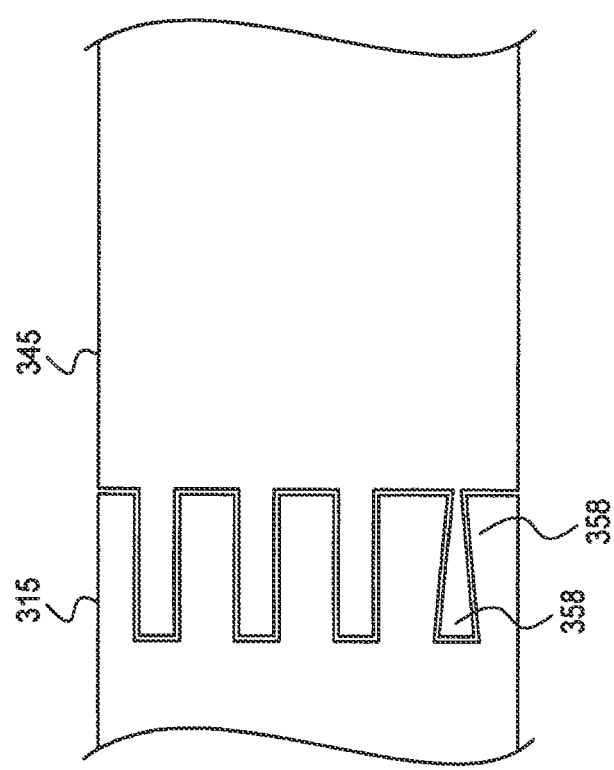
FIG. 28 depicts an enlarged cross sectional view of a radiation sensing device mating with a holder, in accordance with one preferred embodiment of the invention.
Figure 29:
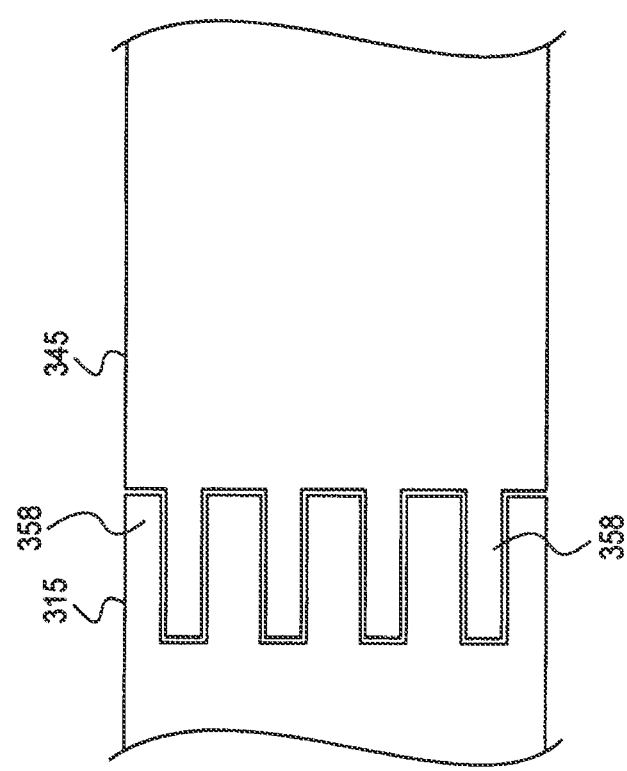
FIG. 29 depicts an enlarged cross sectional view of a radiation sensing device mating with a holder, in accordance with one preferred embodiment of the invention.

In one embodiment, the engagement members 315 and 345 includes such engagement members as a snap-fit engagement, teeth such as a gear tooth or a saw tooth shaped member, or any other type of cooperating member such as fingers. In one embodiment, the engagement members 315 and 345 include teeth 353 which are in a saw-like pattern, as shown in FIG. 26. The teeth 353 intermesh with each other and allow for the engagement members 315 and 345 to slide against each other and lock at more than one preset position. However, in one embodiment, the complementary holder engagement member 315 and the opposing sensor engagement member 345 both include fingers 358 which prevent each other from sliding against each other. The fingers 358 can be keyed, as shown in FIGS. 28, so as to allow on one position in which the engagement members can mate, or they can all be nearly identical, as shown in FIG. 29, so as to allow more than one preset position.

Preferably, the engagement members 315 and 345 are formed of a somewhat flexible material so as to allow movement between the sensor engagement member 345 and the complimentary engagement member 315. Using a flexible material allows the engagement members 315 and 345 to retain contact with each other even when moved or slide with respect to each other. Preferably, the engagement members 315 and 345 are constructed from a rigid yet somewhat flexible material through which radiation can pass, such as but not limited to: metals such as iron, steel, stainless steel, aluminum, silver, titanium, and brass; plastics, such as ethylene, vinyl, acetate; acrylics, such as acrylonitrol-butadine-styrene; resins; and polymers such as polycarbonate.

Radiation sensing device 340 preferably includes a housing 341 which surrounds either the radiation film unit or the radiation sensor unit 344, as shown in FIG. 24. Preferably, the housing 341 completely envelopes the radiation film unit or the radiation sensor unit 344, as shown in FIG. 24, however, the housing 341 may have a window, or a plurality of windows exposing a portion of the radiation film unit or the radiation sensor unit 344. Preferably, the housing 341 is manufactured using an injection molded process in order to reduce costs. However, the housing 341 can be manufactured in one of many ways. For example, housing 341 may be machined, thermoformed, and hand-made. Preferably, in order to reduce costs and maintain rigidity, housing 341 is a one-piece unit which is integrally formed, or a two-piece unit which is snap fitted together. However, housing 341 may comprise multiple parts which are then assembled and fitted together. Preferably, housing 341 is constructed from a rigid yet somewhat flexible material through which radiation can pass, such as but not limited to: metals such as iron, steel, stainless steel, aluminum, silver, titanium, and brass; plastics, such as ethylene, vinyl, acetate; acrylics, such as acrylonitrol-butadine-styrene; resins; and polymers such as polycarbonate. The housing 341 may be colored any one of various different colors depending on the size and type of sensors used. For example, the housing 341 may be colored white for a size two x-ray film unit or colored green for a size zero x-ray film unit.

In one embodiment, the sensor engagement member 345 is connected with the housing 341. In this embodiment, the sensor engagement member 345 can be connected to the housing in any way, such as by using mechanical fasters including hook and loop type fasters such as VELCRO™, projecting members such as keys, channels and cavities such as key-holes, snap-fit arrangements, a frictional arrangement which includes members which frictionally engage each other, screws, nails, nuts and bolts, hydraulic engagement; chemical fasteners such as epoxy or other types of glue, solder or other types of welding engagements; magneto-electrical fasteners such as magnets, electrical magnets, and charged couplings. In one embodiment, the sensor engagement member 345 is integrally connected with and formed as one-piece with the housing 341, as shown in FIG. 24. The sensor engagement member 345 is located on one or more sides of the radiation sensor unit 344. Preferably, the sensor engagement member 345 is located on four sides of the radiation sensor unit 344 and surrounds the radiation sensor unit 344, as shown in FIG. 24, allowing the radiation sensing device 340 to be inserted into the holder 310 in one of a variety of ways. In one embodiment, more than one sensor engagement member 345 is connected with the housing 341.

In one embodiment, the sensor engagement member 345 includes first, second, third and fourth sensor engagement members 346, 348, 350, 352 connected with the housing and surrounding the radiation sensor unit 344, as shown in FIGS. 24 and 26. The holder engagement member 315 includes first and second holder engagement members 320, 322 connected with first and second retention guides 316, 318 to better hold and retain the radiation sensing device 340. Either the first and second sensor engagement members 346, 348 or third and fourth sensor engagement members 350, 352 engage the first and second holder engagement members 320, 322, as shown in FIG. 26. In this manner, the radiation sensing device 340 can be precisely secured with respect to the holder 310 to allow for more precise alignment of the radiation sensing device 340.

In operation, the radiation sensing device 340 is inserted into the retention member 312 of the holder 310 between the first and second retention guides 316, 318, as shown in FIGS. 24-27. During insertion, the sensor engagement member 345 contacts and engages the complimentary holder engagement member 315 at a first preset position. Upon pressing and inserting the radiation sensing device 340 further down into the retention member 312, the sensor engagement member 345 contacts and engages the complimentary holder engagement member 315 at a second preset position, retaining the sensing device 340 further down into the retention member 312. Preferably, more than two preset positions exist and the radiation sensing device 340 can be inserted further down into the retention member 312 and retained at more than two preset positions and preferably at more than three preset positions and more preferably at five or more preset positions. Allowing the radiation sensing device 340 to be retained at more than one preset position within the retention member 312 of the holder 310 offers a used of the system 300 great flexibility in the positioning of the radiation sensing device 340 with respect to the holder 310.

In one embodiment, the system 300 also includes a ring guide adapter 360 connected with the holder 310, a rod 390 removably connected with the ring guide adapter 360, and a ring guide 400 which is slidably connected with the rod 390, as shown in FIG. 24. The ring guide adapter 360 can be connected with any ring guide and radiation sensor holder known or described herein. As shown in FIG. 24, the ring guide adapter 360 is connected with holder 310 at the handle 336. The rod 390 and the ring guide 400 are equivalent to the rod 240 and ring guide 250 described herein. The ring guide adapter 360 includes first, second and third alignment members 362, 368, 374, as shown in FIG. 24.

Each alignment member 362, 368, 374 includes an engagement member 364, 370, 376, respectively, which is removably connected with and mates with a complementary engagement member on the rod 390. The first, second, and third alignment members 362, 368, 374 are positioned in an E-shaped arrangement, as shown in FIG. 24. In this arrangement, the first alignment member 362 is above the second alignment member 368 which is above the third alignment member 374 and which are all connected via a connecting member 383. In this manner, the engagement member on the rod 390 engages each engagement member 364, 370, 376 all at the same side of the ring guide adapter 360, as shown in FIG. 27. All the alignment members 362, 368, 374 are facing away from the retention member 312, as shown in FIG. 24. The ring guide adapter 360 includes a wire retention member 386 which is preferably positioned on the second alignment member 368 adjacent the handle 336, as shown in FIG. 24. Preferably, the first, second, and third alignment members 362, 368, 374 are positioned on the ring guide adapter 360 so that when the rod 390 is removably connected with the second alignment member 368, the ring guide 400 is positioned for a first radiograph type, such as a bite wing or anterior type radiograph; so that when rod 390 is removably connected with the third alignment member 374, the ring guide 400 is positioned for a second radiograph type, such as a lower posterior type radiograph; and so that when rod 390 is removably connected with the first alignment member 362, the ring guide 400 is positioned for a third radiograph type, such as a upper posterior type radiograph.

Figure 30:
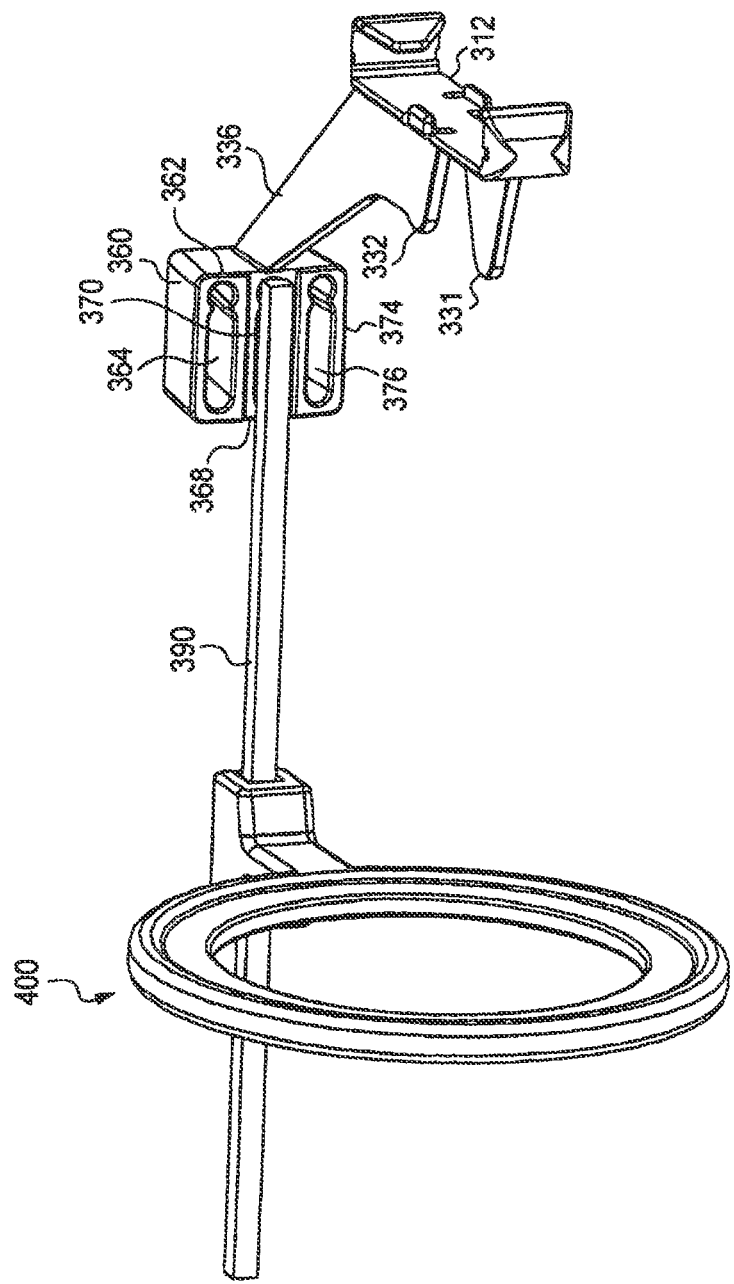
FIG. 30 depicts a perspective view of a ring guide adapter connected with a holder for holding a radiation sensing device and a ring guide, in accordance with one preferred embodiment of the invention.
Figure 31:
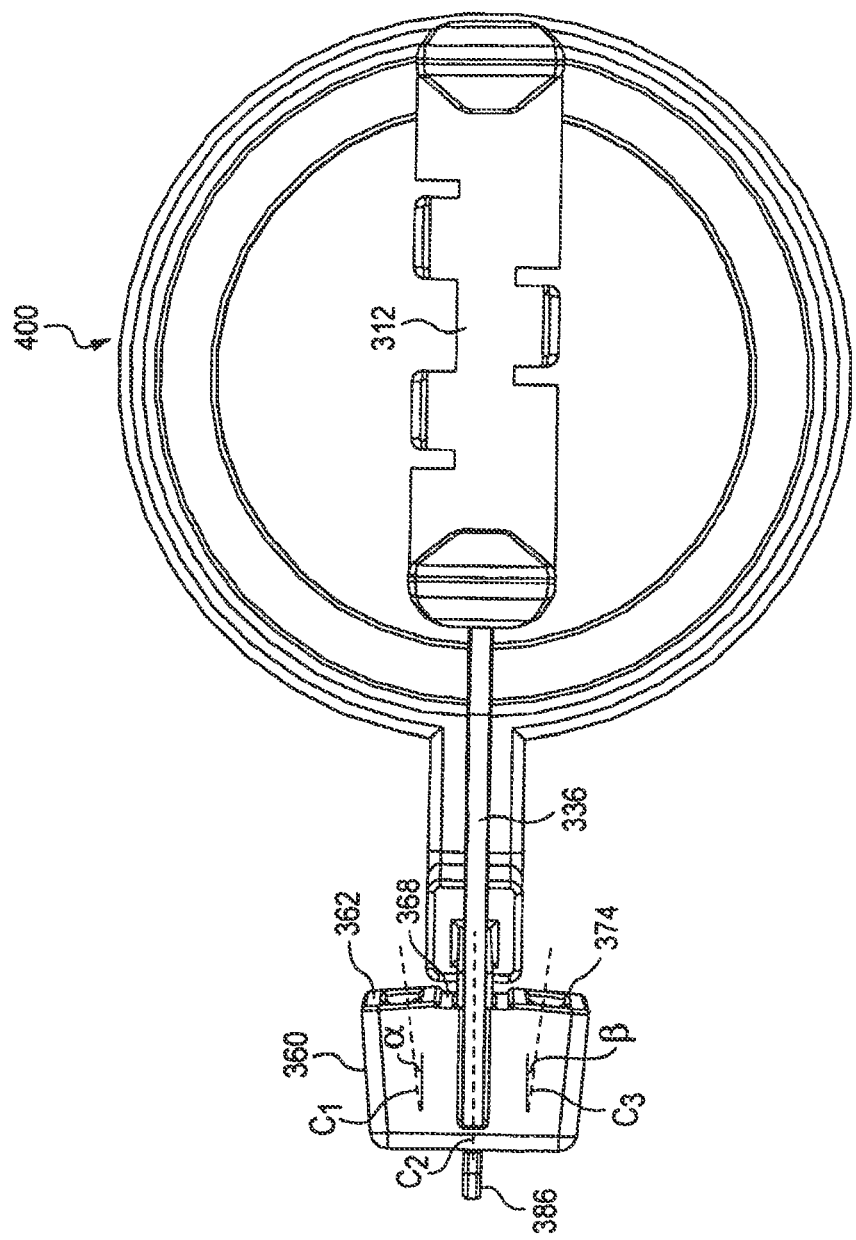
FIG. 31 depicts an enlarged frontal view of ring guide adapter shown in FIG. 30, in accordance with one preferred embodiment of the invention.

In one embodiment, the first, second, and third alignment members 362, 368, 374 are positioned in an E-shaped arrangement, wherein all the alignment members 362, 368, 374 are facing towards the retention member 312, as shown in FIG. 30. In this arrangement, the first alignment member 362 is above and connected with the second alignment member 368 which is above and connected with the third alignment member 374. In this manner, the engagement member on the rod 390 engages each engagement member 364, 370, 376 all at the side of the ring guide adapter 360 which faces towards the retention member 312, as shown in FIG. 30. Preferably, the alignment members 362, 368, 374 are positioned adjacent each other in a stacked configuration, as shown in FIGS. 30 and 31. The first, second, and third alignment members 362, 368, 374 are positioned on the ring guide adapter 360 so that when the rod 390 is removably connected with the second alignment member 368, the ring guide 400 is positioned for a first radiograph type, such as a bite wing or anterior type radiograph; so that when rod 390 is removably connected with the third alignment member 374, the ring guide 400 is positioned for a second radiograph type, such as a lower posterior type radiograph; and so that when rod 390 is removably connected with the first alignment member 362, the ring guide 400 is positioned for a third radiograph type, such as a upper posterior type radiograph.

As shown in FIG. 31, the first alignment member 362 is aligned along a first centerline $C_1$, the second alignment member 368 is aligned along a second centerline $C_2$, and the third alignment member 374 is aligned along a third centerline $C_3$. An angle $\alpha$ is formed between the first and second alignment members 362, 368 and more specifically between the first and second centerlines $C_1$, $C_2$. Preferably, the angle $\alpha$ is chosen so as to precisely position the ring guide 400 for a second radiograph type. An angle $\beta$ is formed between the second and third alignment members 368, 374 and more specifically between the second and third centerlines $C_2$, $C_3$. Preferably, the angle $\beta$ is chosen so as to precisely position the ring guide 400 for third radiograph types. Preferably, the angle $\alpha$ is between 5 and 90 degrees, and more preferably between 10 and 30 degrees, and most preferably about 15 degrees. Preferably, the angle $\beta$ is between 5 and 90 degrees, and more preferably between 10 and 30 degrees, and most preferably about 15 degrees. Such positioning of the first, second, and third alignment members 362, 368, 374 allows for a more compact arrangement of the ring guide adapter 360.

Figure 32:
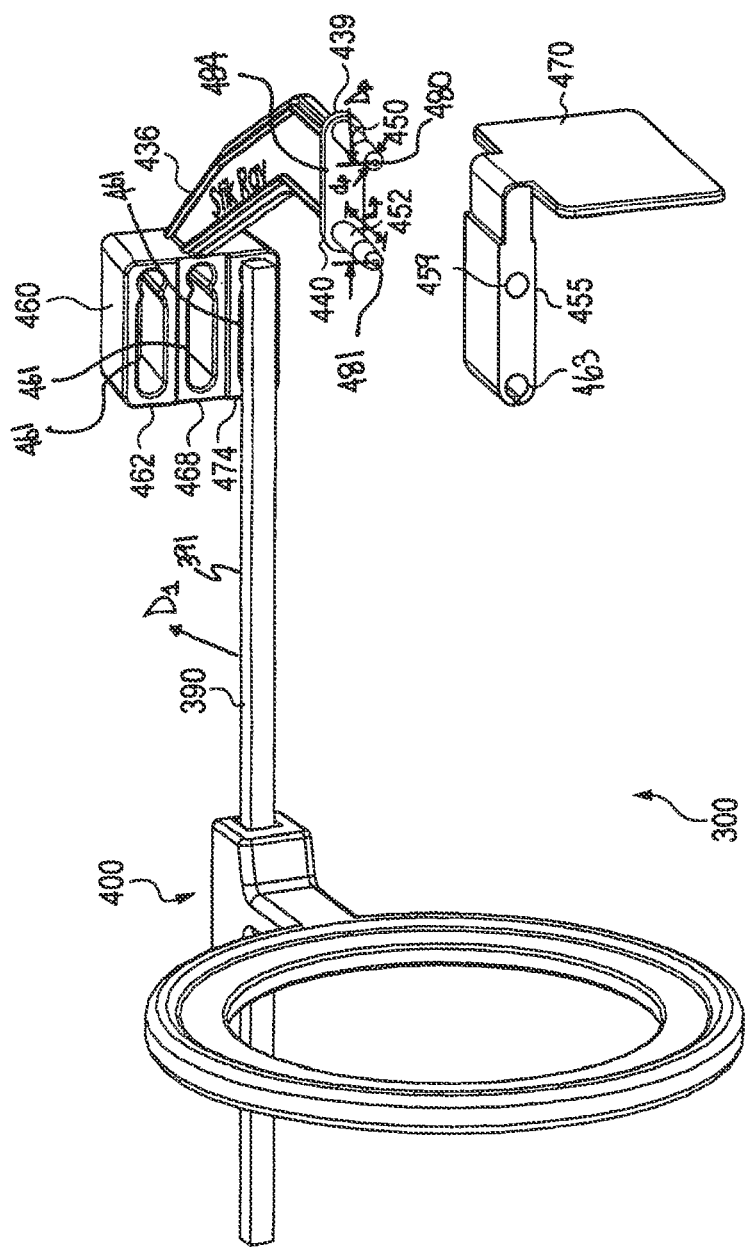
FIG. 32 depicts a perspective view of a ring guide adapter connected with a holder for holding a radiation sensing device and a ring guide, in accordance with one preferred embodiment of the invention.
Figure 33:
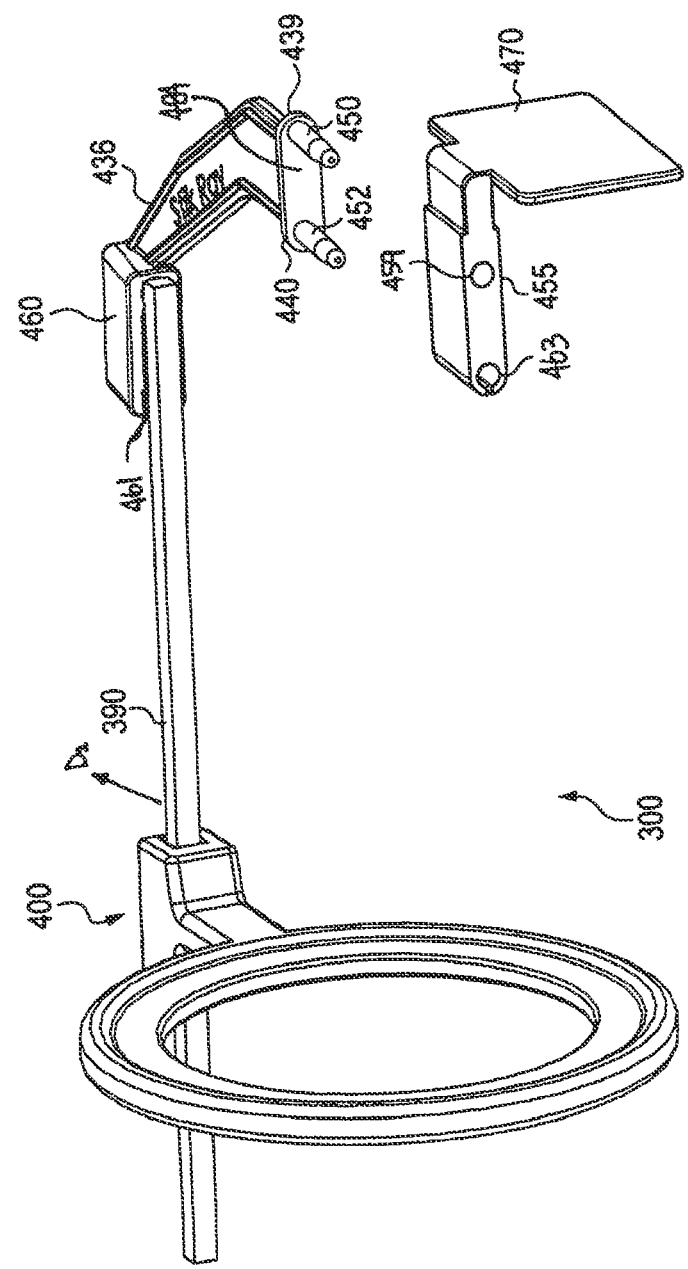
FIG. 33 depicts a perspective view of an engagement member connected with a holder for holding a radiation sensing device and a ring guide, in accordance with one preferred embodiment of the invention.

In one embodiment, the system 300 includes a ring guide adapter 460 removably connected with a holder 470 for holding a radiation sensing device 120, a rod 390 removably connected with the ring guide adapter 460, and a ring guide 400 which is slidably connected with the rod 390, as shown in FIGS. 32 and 33. The ring guide adapter 460 includes an engagement member 461. Engagement member 461 is configured to removably connect with and engage a complementary engagement member 241 on the rod 390. In one embodiment, complimentary engagement member 241 includes a pair of projections 242, 244 extending from the rod 390 in a direction $D_1$ which is normal to a surface 391 of the rod 390 of the engagement member 241. In this embodiment, engagement member 241 forms a large cavity 500, or a pair of cavities 501, 502, for receiving the pair of projections 242, 244 extending from the rod 390.

In one embodiment, the ring guide adapter 460 includes an engagement member 440 connected with the engagement member 461 through a handle 436. Handle 436 connects the ring guide adapter 460 with engagement member 440. Preferably, handle 436 extends up and away from the ring guide adapter 460, as shown in FIG. 32. At one end the handle 436 is connected with the ring guide adapter 460 and at an opposing end 439 the handle 436 is connected with an engagement member 440 which engages another device, such as a holder 470, or a bite wing adapter, and specifically engages a complimentary engagement member 455 on the devices, such as holder 470.

As used herein, an engagement member, such as the engagement members 461, 440 and 455, may be any device which is adapted to removably connect with another device, and includes such thing as: mechanical fasters including hook and loop type fasters such as VELCRO™, projecting members such as keys, channels and cavities such as key-holes, snap-fit arrangements, a frictional arrangement which includes members which frictionally engage each other, screws, nails, nuts and bolts, hydraulic engagement; chemical fasteners such as epoxy or other types of glue, solder or other types of welding engagements; magneto-electrical fasteners such as magnets, electrical magnets, and charged couplings.

In one embodiment, the engagement member 440 includes a pair of projecting members 450, 452 projecting from a base 484 of engagement member 440 and which mate with and engage channels 459, 463 formed in complimentary engagement member 455, as shown in FIG. 32. Projecting members 450, 452 project in a direction which is generally normal from the base 484. Projecting members 452, 450 are generally cylindrical in shape and are spaced apart from each other by a distance $D_p$. By mating with engagement member 455, engagement member 440 can be used to mate with a variety of holders for holding a radiation sensing device, such as holder 470, which have engagement member 455. Preferably, projecting members 450, 452 have the same general size, length, and placement as the pair of projections 242, 244 extending from the rod 390. Preferably, the projecting members 450, 452 have a diameter $d_p$ of between 1 mm and 10 mm, and preferably between 2 mm and 5 mm, and most preferably between 2.5 mm and 3.5 mm, and even more preferably approximately 3 mm, ±10%. Preferably, projecting members 450, 452 have a length $L_p$ of between 5 mm and 20 mm, and preferably between 8 mm and 15 mm, and most preferably between 11 mm and 13 mm, and even more preferably approximately 12 mm, ±10%. Preferably, the distance $D_p$ between center points 480, 481 of projecting members 450, 452 is between 5 mm and 20 mm, and preferably between 8 mm and 15 mm, and most preferably between 12 mm and 14 mm, and even more preferably approximately 13.1 mm, ±10%. Engagement member 440 may be part of adapter 460 and connected with engagement member 461, or engagement member 440 can be part of any dental instrument and connected with any type of dental adapter, radiation sensor holder, rod, handle, or bite block.

In one embodiment, the ring guide adapter 460 includes first, second and third alignment members 462, 468, 474, as shown in FIG. 32. Each alignment member 462, 468, 474 includes an engagement member 461 which is removably connected with and mates with a complementary engagement member 241 on the rod 390. The first, second, and third alignment members 362, 368, 374 are positioned in any one of a number of arrangements, such as: an E-shaped arrangement, as shown in FIG. 32; a Y-shaped arrangement, as shown in FIG. 22; or a C-shaped arrangement, as shown in FIG. 31. In the E-shaped arrangement, the first alignment member 462 is above the second alignment member 468 which is above the third alignment member 474. In this manner, the engagement member on the rod 390 engages each engagement member on the adapter 460 all at the same side of the ring guide adapter 460, as shown in FIG. 32. The ring guide adapter 360 preferably includes a wire retention member (not shown).

In one embodiment, the ring guide adapter 460 and/or any of the components described herein, such as engagement member 461, handle 436, engagement member 440, projecting members 450, 452, first, second and third alignment members 462, 468, 474, are integrally formed as one piece with any combination of other components. In one embodiment, the ring guide adapter 460 and/or any of the components described herein, such as engagement member 461, handle 436, engagement member 440, projecting members 450, 452, first, second and third alignment members 462, 468, 474, are constructed from a rigid yet somewhat flexible material, such as but not limited to a metal such as iron, steel, stainless steel, aluminum, silver, titanium, and brass; a polymer such as ethylene, vinyl, acetate, acrylics, acrylonitrol-butadine-styrene, resin, polycarbonate, polypropylene, acrylonitrile butadiene styrene (ABS), polysulphone, or any autoclavable polymer which can withstand temperatures of in excess of 240° for at least three minutes.

In one embodiment, projecting members 450, 452 comprise an autoclavable polymer which can withstand temperatures of in excess of 240° F. for at least three minutes. Preferably, the autoclavable polymer is one of polycarbonate, polypropylene, acrylonitrile butadiene styrene (ABS), or polysulphone. More preferably, the autoclavable polymer is Ineos H13M-00 polypropylene. Using an autoclavable polymer for the projecting members 450, 452 allows projecting members 450, 452 to be formed at lower cost than if the projecting members 450, 452 were formed from a metal. Additionally, using an autoclavable polymer for the projecting members 450, 452 still allows projecting members 450, 452 to maintain alignment with engagement members, such as complimentary engagement sensor member 455. In one embodiment, projecting member 450, 452 comprise an autoclavable polymer, are autoclaved, and then are matted with complimentary engagement member 455. When autoclaving projecting member 450, 452, projecting member 450, 452 are subjected to temperatures of 240° F. or greater, and preferably 250° F. or greater, and more preferably temperatures from 240° F. to 300° F., and most preferably temperatures from 250° F. to 280° F., for at least from three to fifteen minutes. Projecting member 450, 452 are autoclaved at a pressure of between 150 and 200 kilopascals, and preferably about 186 kilopascals, ±10%. Upon autoclaving projecting members 450, 452, projecting members 450, 452 are mated with and engage channels 459, 463 formed in the complimentary engagement member 455. Upon autoclaving, the tolerance is maintained between the projecting members 450, 452 and channels 459, 463 formed in the complimentary engagement member 455, so as to allow for engagement between the projecting members 450, 452 and channels 459, 463.

For example, the engagement member 440 has an initial tolerance, for all of its parts (i.e. projections 450, 452 and base 484) and their locations with respect to each other, so that first and second projecting members 450, 452 are able to engage and mate with channels 459, 463 formed in a complimentary engagement member 455. Upon autoclaving the engagement member 440, a resulting tolerance of the engagement member 440, and its subsequent parts and their locations, is maintained to within ±10% of the engagement member 440's initial tolerance, so as to allow for continued engagement between the first and second projecting members 450, 452 and channels 459, 463 formed in a complimentary engagement member 455. Although the invention has been described and illustrated with reference to specific illustrative embodiments thereof, it is not intended that the invention be limited to those illustrative embodiments. Those skilled in the art will recognize that variations and modifications can be made without departing from the spirit of the invention.

What is claim is:

1. An engagement system for connecting an engagement member with an engaged device, the engagement system comprising:
    an engaged device having a complimentary engagement member, wherein the engaged device is one of a dental adapter, a radiation sensor holder, a rod which engages a ring guide at one end, a handle, and a bite block; and
    an engagement member having
        a planar base having a first side, and a second side opposite the first side;
        a flat handle coupled to the planar base along a portion of a width of the first side of the planar base, the handle extending away from the first side of the planar base in a normal direction relative to the planar base;
        a first projecting member projecting in a normal direction from the second side of the planar base and projecting away from the second side of the planar base in a direction opposite to that of the handle;
        a second projecting member spaced apart from the first projecting member and projecting from the second side of the planar base in a direction parallel to the first projecting member and projecting away from the second side of the planar base in the direction opposite to that of the handle;
        the first and second projecting members disposed at opposite ends of the planar base; and
    wherein the first and second projecting members comprise an autoclavable polymer, wherein the base and the first and second projecting members are one-piece, and wherein the first and second projecting members are removably received within corresponding channels formed in the complementary engagement member.

2. The engagement member of claim 1, wherein the autoclavable polymer withstands temperatures in excess of 240° F. for at least three minutes.

3. The engagement member of claim 1, wherein each projecting member has a diameter $d_p$ of between 1 mm and 10 mm and a length $L_p$ of between 5 mm and 20 mm.

4. The engagement member of claim 1, wherein each projecting member has a center point at a center of each projecting member along a cross section, and wherein a distance $D_p$ between the center points is between 5 mm and 20 mm.

5. The engagement member of claim 1, wherein the engagement member is connected with a second engagement member forming a pair of cavities for receiving a pair of projections.

6. The engagement member of claim 1, wherein the autoclavable polymer is one of polycarbonate, polypropylene, acrylonitrile butadiene styrene (ABS), or polysulphone.

7. The engagement member of claim 1, wherein the engagement member has an initial tolerance, wherein upon autoclaving the engagement member a resulting tolerance of the engagement member is maintained to within ±10% of the engagement member's initial tolerance, so as to allow for continued engagement between the first and second projecting members and channels formed in the complimentary engagement member.

8. An engagement system for connecting an engagement member with an engaged device, the engagement system comprising:
   an engaged device having a complimentary engagement member, wherein the engaged device is one of a dental adapter, a radiation sensor holder, a rod which engages a ring guide at one end, a handle, and a bite block; and
   an engagement member having
      a planar base having a first side, and a second side opposite the first side;
      a flat handle coupled to the planar base along a portion of a width of the first side of the planar base, the handle extending away from the first side of the planar base in a normal direction relative to the planar base;
      a first projecting member projecting in a first direction from the second side of the planar base and projecting away from the second side of the planar base in a direction generally opposite to that of the handle;
      a second projecting member spaced apart from the first projecting member and projecting from the second side of the planar base in generally the same direction from the base as the first projecting member and projecting away from the second side of the planar base in the direction generally opposite to that of the handle;
      the first and second projecting members disposed at opposite lateral ends of the planar base;
      wherein the first and second projecting members comprise an autoclavable polymer, and wherein the first and second projecting members are removably engaged within corresponding channels formed in the complementary engagement member.

9. The engagement member of claim 8, wherein the autoclavable polymer withstands temperatures in excess of 240° F. for at least three minutes.

10. The engagement member of claim 8, wherein each projecting member has a diameter $d_p$ of between 1 mm and 10 mm and a length $L_p$ of between 5 mm and 20 mm.

11. The engagement member of claim 8, wherein each projecting member has a center point at a center of each projecting member along a cross section, and wherein a distance $D_p$ between the center points is between 5 mm and 20 mm.

12. The engagement member of claim 8, wherein the engagement member is connected with a second engagement member forming a pair of cavities for receiving a pair of projections.

13. The engagement member of claim 8, wherein the autoclavable polymer is one of polycarbonate, polypropylene, acrylonitrile butadiene styrene (ABS), or polysulphone.

14. The engagement member of claim 8, wherein the engagement member has an initial tolerance, wherein upon autoclaving the engagement member a resulting tolerance of the engagement member is maintained to within ±10% of the engagement member's initial tolerance, so as to allow for continued engagement between the first and second projecting members and channels formed in the complimentary engagement member.

* * * * *